United States Patent [19]

Evans et al.

[11] Patent Number: 5,696,233

[45] Date of Patent: Dec. 9, 1997

[54] ORPHAN STEROID HORMONE RECEPTORS

[75] Inventors: Ronald M. Evans, La Jolla; David J. Mangelsdorf, San Diego; Estelita S. Ong, San Diego; Anthony E. Oro, San Diego, all of Calif.; Uwe K. Borgmeyer, Hamburg, Germany; Vincent Giguere, Etobicoke, Canada; Tso-Pang Yao, San Diego, Calif.

[73] Assignee: The Salk Institute for Biological Studies, La Jolla, Calif.

[21] Appl. No.: 463,694

[22] Filed: Jun. 5, 1995

Related U.S. Application Data

[62] Division of Ser. No. 333,358, Nov. 2, 1994, Pat. No. 5,571,696, which is a continuation of Ser. No. 761,068, Sep. 17, 1991, abandoned.

[51] Int. Cl.$^6$ ............................................. C07K 14/72
[52] U.S. Cl. ....................................... 530/350; 530/358
[58] Field of Search ................................ 530/350, 399, 530/358

[56] References Cited

PUBLICATIONS

Baker et al. PNAS 85(1988) 3294–3298.
Beato Cell 56 (1989) 335–344.
Evans Science 240(1988) 889–895.
Mangelsdorf et al. Nature 345 (1990) 224–229.

*Primary Examiner*—Paula K. Hutzell
*Assistant Examiner*—Robert C. Hayes
*Attorney, Agent, or Firm*—Gray Cary Ware & Freidenrich; Stephen E. Reiter

[57] ABSTRACT

Novel members of the steroid/thyroid superfamily of receptors are described. DNA sequences encoding same, expression vectors containing such DNA and host cells transformed with such expression vectors are also disclosed, as are methods for the expression of the novel receptors of the invention, and various uses thereof.

20 Claims, 1 Drawing Sheet

Correlation of XR1 Alternate Splicing Products 5,696,233

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1952 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR1 (VERHT19.SEQ)

( i x ) FEATURE:
        ( A ) NAME/KEY: CDS
        ( B ) LOCATION: 79..1725

( i x ) FEATURE:
        ( A ) NAME/KEY: misc_feature
        ( B ) LOCATION: 349..1952
        ( D ) OTHER INFORMATION: /product="Carboxy terminal portion of XR1 variant verht3"

( i x ) FEATURE:
        ( A ) NAME/KEY: misc_feature
        ( B ) LOCATION: 352..1952
        ( D ) OTHER INFORMATION: /product="Carboxy terminal portion of XR1 variant verhr5"

( x i ) SEQUENCE DESCRIPTION: SEQ ID NO:1:

```
GAATTCGGGG ACTCCATAGT ACACTGGGGC AAAGCACAGC CCCAGTTTCT GGAGGCAGAT        60

GGGTAACCAG GAAAAGGC ATG AAT GAG GGG GCC CCA GGA GAC AGT GAC TTA       111
                    Met Asn Glu Gly Ala Pro Gly Asp Ser Asp Leu
```

```
                                    1                        5                            10
GAG  ACT  GAG  GCA  AGA  GTG  CCG  TGG  TCA  ATC  ATG  GGT  CAT  TGT  CTT  CGA       159
Glu  Thr  Glu  Ala  Arg  Val  Pro  Trp  Ser  Ile  Met  Gly  His  Cys  Leu  Arg
               15                       20                       25

ACT  GGA  CAG  GCC  AGA  ATG  TCT  GCC  ACA  CCC  ACA  CCT  GCA  GGT  GAA  GGA       207
Thr  Gly  Gln  Ala  Arg  Met  Ser  Ala  Thr  Pro  Thr  Pro  Ala  Gly  Glu  Gly
          30                       35                       40

GCC  AGA  AGC  TCT  TCA  ACC  TGT  AGC  TCC  CTG  AGC  AGG  CTG  TTC  TGG  TCT       255
Ala  Arg  Ser  Ser  Ser  Thr  Cys  Ser  Ser  Leu  Ser  Arg  Leu  Phe  Trp  Ser
     45                       50                       55

CAA  CTT  GAG  CAC  ATA  AAC  TGG  GAT  GGA  GCC  ACA  GCC  AAG  AAC  TTT  ATT       303
Gln  Leu  Glu  His  Ile  Asn  Trp  Asp  Gly  Ala  Thr  Ala  Lys  Asn  Phe  Ile
60                       65                       70                       75

AAT  TTA  AGG  GAG  TTC  TTC  TCT  TTT  CTG  CTC  CCT  GCA  TTG  AGA  AAA  GCT       351
Asn  Leu  Arg  Glu  Phe  Phe  Ser  Phe  Leu  Leu  Pro  Ala  Leu  Arg  Lys  Ala
                    80                       85                       90

CAA  ATT  GAA  ATT  ATT  CCA  TGC  AAG  ATC  TGT  GGA  GAC  AAA  TCA  TCA  GGA       399
Gln  Ile  Glu  Ile  Ile  Pro  Cys  Lys  Ile  Cys  Gly  Asp  Lys  Ser  Ser  Gly
               95                      100                      105

ATC  CAT  TAT  GGT  GTC  ATT  ACA  TGT  GAA  GGC  TGC  AAG  GGC  TTT  TTC  AGG       447
Ile  His  Tyr  Gly  Val  Ile  Thr  Cys  Glu  Gly  Cys  Lys  Gly  Phe  Phe  Arg
          110                      115                      120

AGA  AGT  CAG  CAA  AGC  AAT  GCC  ACC  TAC  TCC  TGT  CCT  CGT  CAG  AAG  AAC       495
Arg  Ser  Gln  Gln  Ser  Asn  Ala  Thr  Tyr  Ser  Cys  Pro  Arg  Gln  Lys  Asn
125                      130                      135

TGT  TTG  ATT  GAT  CGA  ACC  AGT  AGA  AAC  CGC  TGC  CAA  CAC  TGT  CGA  TTA       543
Cys  Leu  Ile  Asp  Arg  Thr  Ser  Arg  Asn  Arg  Cys  Gln  His  Cys  Arg  Leu
140                      145                      150                      155

CAG  AAA  TGC  CTT  GCC  GTA  GGG  ATG  TCT  CGA  GAT  GCT  GTA  AAA  TTT  GGC       591
Gln  Lys  Cys  Leu  Ala  Val  Gly  Met  Ser  Arg  Asp  Ala  Val  Lys  Phe  Gly
               160                      165                      170

CGA  ATG  TCA  AAA  AAG  CAG  AGA  GAC  AGC  TTG  TAT  GCA  GAA  GTA  CAG  AAA       639
Arg  Met  Ser  Lys  Lys  Gln  Arg  Asp  Ser  Leu  Tyr  Ala  Glu  Val  Gln  Lys
          175                      180                      185

CAC  CGG  ATG  CAG  CAG  CAG  CAG  CGC  GAC  CAC  CAG  CAG  CAG  CCT  GGA  GAG       687
His  Arg  Met  Gln  Gln  Gln  Gln  Arg  Asp  His  Gln  Gln  Gln  Pro  Gly  Glu
     190                      195                      200

GCT  GAG  CCG  CTG  ACG  CCC  ACC  TAC  AAC  ATC  TCG  GCC  AAC  GGG  CTG  ACG       735
Ala  Glu  Pro  Leu  Thr  Pro  Thr  Tyr  Asn  Ile  Ser  Ala  Asn  Gly  Leu  Thr
205                      210                      215

GAA  CTT  CAC  GAC  GAC  CTC  AGT  AAC  TAC  ATT  GAC  GGG  CAC  ACC  CCT  GAG       783
Glu  Leu  His  Asp  Asp  Leu  Ser  Asn  Tyr  Ile  Asp  Gly  His  Thr  Pro  Glu
220                      225                      230                      235

GGG  AGT  AAG  GCA  GAC  TCC  GCC  GTC  AGC  AGC  TTC  TAC  CTG  GAC  ATA  CAG       831
Gly  Ser  Lys  Ala  Asp  Ser  Ala  Val  Ser  Ser  Phe  Tyr  Leu  Asp  Ile  Gln
               240                      245                      250

CCT  TCC  CCA  GAC  CAG  TCA  GGT  CTT  GAT  ATC  AAT  GGA  ATC  AAA  CCA  GAA       879
Pro  Ser  Pro  Asp  Gln  Ser  Gly  Leu  Asp  Ile  Asn  Gly  Ile  Lys  Pro  Glu
          255                      260                      265

CCA  ATA  TGT  GAC  TAC  ACA  CCA  GCA  TCA  GGC  TTC  TTT  CCC  TAC  TGT  TCG       927
Pro  Ile  Cys  Asp  Tyr  Thr  Pro  Ala  Ser  Gly  Phe  Phe  Pro  Tyr  Cys  Ser
          270                      275                      280

TTC  ACC  AAC  GGC  GAG  ACT  TCC  CCA  ACT  GTG  TCC  ATG  GCA  GAA  TTA  GAA       975
Phe  Thr  Asn  Gly  Glu  Thr  Ser  Pro  Thr  Val  Ser  Met  Ala  Glu  Leu  Glu
285                      290                      295

CAC  CTT  GCA  CAG  AAT  ATA  TCT  AAA  TCG  CAT  CTG  GAA  ACC  TGC  CAA  TAC      1023
His  Leu  Ala  Gln  Asn  Ile  Ser  Lys  Ser  His  Leu  Glu  Thr  Cys  Gln  Tyr
300                      305                      310                      315

TTG  AGA  GAA  GAG  CTC  CAG  CAG  ATA  ACG  TGG  CAG  ACC  TTT  TTA  CAG  GAA      1071
Leu  Arg  Glu  Glu  Leu  Gln  Gln  Ile  Thr  Trp  Gln  Thr  Phe  Leu  Gln  Glu
```

|  |  |  |  |  |  |  |  |  |  |  |  |  |  |  |  |
|---|---|---|---|---|---|---|---|---|---|---|---|---|---|---|---|
|  |  |  | 320 |  |  |  |  | 325 |  |  |  |  | 330 |  |  |
| GAA | ATT | GAG | AAC | TAT | CAA | AAC | AAG | CAG | CGG | GAG | GTG | ATG | TGG | CAA | TTG | 1119 |
| Glu | Ile | Glu | Asn 335 | Tyr | Gln | Asn | Lys | Gln 340 | Arg | Glu | Val | Met | Trp 345 | Gln | Leu |  |
| TGT | GCC | ATC | AAA | ATT | ACA | GAA | GCT | ATA | CAG | TAT | GTG | GTG | GAG | TTT | GCC | 1167 |
| Cys | Ala | Ile 350 | Lys | Ile | Thr | Glu | Ala | Ile 355 | Gln | Tyr | Val | Val 360 | Glu | Phe | Ala |  |
| AAA | CGC | ATT | GAT | GGA | TTT | ATG | GAA | CTG | TGT | CAA | AAT | GAT | CAA | ATT | GTG | 1215 |
| Lys | Arg 365 | Ile | Asp | Gly | Phe | Met 370 | Glu | Leu | Cys | Gln | Asn | Asp 375 | Gln | Ile | Val |  |
| CTT | CTA | AAA | GCA | GGT | TCT | CTA | GAG | GTG | GTG | TTT | ATC | AGA | ATG | TGC | CGT | 1263 |
| Leu 380 | Leu | Lys | Ala | Gly | Ser 385 | Leu | Glu | Val | Val | Phe 390 | Ile | Arg | Met | Cys | Arg 395 |  |
| GCC | TTT | GAC | TCT | CAG | AAC | AAC | ACC | GTG | TAC | TTT | GAT | GGG | AAG | TAT | GCC | 1311 |
| Ala | Phe | Asp | Ser | Gln 400 | Asn | Asn | Thr | Val | Tyr 405 | Phe | Asp | Gly | Lys | Tyr 410 | Ala |  |
| AGC | CCC | GAC | GTC | TTC | AAA | TCC | TTA | GGT | TGT | GAA | GAC | TTT | ATT | AGC | TTT | 1359 |
| Ser | Pro | Asp | Val 415 | Phe | Lys | Ser | Leu | Gly 420 | Cys | Glu | Asp | Phe | Ile 425 | Ser | Phe |  |
| GTG | TTT | GAA | TTT | GGA | AAG | AGT | TTA | TGT | TCT | ATG | CAC | CTG | ACT | GAA | GAT | 1407 |
| Val | Phe | Glu 430 | Phe | Gly | Lys | Ser | Leu 435 | Cys | Ser | Met | His | Leu 440 | Thr | Glu | Asp |  |
| GAA | ATT | GCA | TTA | TTT | TCT | GCA | TTT | GTA | CTG | ATG | TCA | GCA | GAT | CGC | TCA | 1455 |
| Glu | Ile | Ala 445 | Leu | Phe | Ser | Ala | Phe 450 | Val | Leu | Met | Ser | Ala 455 | Asp | Arg | Ser |  |
| TGG | CTG | CAA | GAA | AAG | GTA | AAA | ATT | GAA | AAA | CTG | CAA | CAG | AAA | ATT | CAG | 1503 |
| Trp 460 | Leu | Gln | Glu | Lys | Val 465 | Lys | Ile | Glu | Lys | Leu 470 | Gln | Gln | Lys | Ile | Gln 475 |  |
| CTA | GCT | CTT | CAA | CAC | GTC | CTA | CAG | AAG | AAT | CAC | CGA | GAA | GAT | GGA | ATA | 1551 |
| Leu | Ala | Leu | Gln | His 480 | Val | Leu | Gln | Lys | Asn 485 | His | Arg | Glu | Asp | Gly 490 | Ile |  |
| CTA | ACA | AAG | TTA | ATA | TGC | AAG | GTG | TCT | ACA | TTA | AGA | GCC | TTA | TGT | GGA | 1599 |
| Leu | Thr | Lys | Leu 495 | Ile | Cys | Lys | Val | Ser 500 | Thr | Leu | Arg | Ala | Leu 505 | Cys | Gly |  |
| CGA | CAT | ACA | GAA | AAG | CTA | ATG | GCA | TTT | AAA | GCA | ATA | TAC | CCA | GAC | ATT | 1647 |
| Arg | His | Thr 510 | Glu | Lys | Leu | Met | Ala 515 | Phe | Lys | Ala | Ile | Tyr 520 | Pro | Asp | Ile |  |
| GTG | CGA | CTT | CAT | TTT | CCT | CCA | TTA | TAC | AAG | GAG | TTG | TTC | ACT | TCA | GAA | 1695 |
| Val | Arg 525 | Leu | His | Phe | Pro 530 | Pro | Leu | Tyr | Lys | Glu 535 | Leu | Phe | Thr | Ser | Glu |  |
| TTT | GAG | CCA | GCA | ATG | CAA | ATT | GAT | GGG | TAAATGTTAT | | | CACCTAAGCA | | | | 1742 |
| Phe 540 | Glu | Pro | Ala | Met | Gln 545 | Ile | Asp | Gly |  |  |  |  |  |  |  |  |

| CTTCTAGAAT | GTCTGAAGTA | CAAACATGAA | AAACAAACAA | AAAAATTAAC | CGAGACACTT | 1802 |
|---|---|---|---|---|---|---|
| TATATGGCCC | TGCACAGACC | TGGAGCGCCA | CACACTGCAC | ATCTTTTGGT | GATCGGGGTC | 1862 |
| AGGCAAAGGA | GGGGAAACAA | TGAAAACAAA | TAAAGTTGAA | CTTGTTTTTC | TCAAAAAAAA | 1922 |
| AAAAAAAAAA | AAAAAAAAAA | AAAAAAAAA |  |  |  | 1952 |

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asn | Glu | Gly | Ala | Pro | Gly | Asp | Ser | Asp | Leu | Glu | Thr | Glu | Ala | Arg |
|---|---|---|---|---|---|---|---|---|---|---|---|---|---|---|---|
| 1 |  |  |  | 5 |  |  |  |  | 10 |  |  |  |  | 15 |  |

-continued

| | | | | | | | | | | | | | | |
|---|---|---|---|---|---|---|---|---|---|---|---|---|---|---|
| Val | Pro | Trp | Ser 20 | Ile | Met | Gly | His | Cys 25 | Leu | Arg | Thr | Gly | Gln 30 | Ala | Arg |
| Met | Ser | Ala 35 | Thr | Pro | Thr | Pro | Ala 40 | Gly | Glu | Gly | Ala | Arg 45 | Ser | Ser | Ser |
| Thr | Cys 50 | Ser | Ser | Leu | Ser | Arg 55 | Leu | Phe | Trp | Ser | Gln 60 | Leu | Glu | His | Ile |
| Asn 65 | Trp | Asp | Gly | Ala | Thr 70 | Ala | Lys | Asn | Phe | Ile 75 | Asn | Leu | Arg | Glu | Phe 80 |
| Phe | Ser | Phe | Leu | Leu 85 | Pro | Ala | Leu | Arg | Lys 90 | Ala | Gln | Ile | Glu | Ile 95 | Ile |
| Pro | Cys | Lys | Ile 100 | Cys | Gly | Asp | Lys | Ser 105 | Ser | Gly | Ile | His | Tyr 110 | Gly | Val |
| Ile | Thr | Cys 115 | Glu | Gly | Cys | Lys | Gly 120 | Phe | Phe | Arg | Arg | Ser 125 | Gln | Gln | Ser |
| Asn | Ala 130 | Thr | Tyr | Ser | Cys | Pro 135 | Arg | Gln | Lys | Asn | Cys 140 | Leu | Ile | Asp | Arg |
| Thr 145 | Ser | Arg | Asn | Arg | Cys 150 | Gln | His | Cys | Arg | Leu 155 | Gln | Lys | Cys | Leu | Ala 160 |
| Val | Gly | Met | Ser | Arg 165 | Asp | Ala | Val | Lys | Phe 170 | Gly | Arg | Met | Ser | Lys 175 | Lys |
| Gln | Arg | Asp | Ser 180 | Leu | Tyr | Ala | Glu | Val 185 | Gln | Lys | His | Arg | Met 190 | Gln | Gln |
| Gln | Gln | Arg 195 | Asp | His | Gln | Gln | Pro 200 | Gly | Glu | Ala | Glu 205 | Pro | Leu | Thr |
| Pro | Thr 210 | Tyr | Asn | Ile | Ser | Ala 215 | Asn | Gly | Leu | Thr | Glu 220 | Leu | His | Asp | Asp |
| Leu 225 | Ser | Asn | Tyr | Ile | Asp 230 | Gly | His | Thr | Pro | Glu 235 | Gly | Ser | Lys | Ala | Asp 240 |
| Ser | Ala | Val | Ser | Ser 245 | Phe | Tyr | Leu | Asp | Ile 250 | Gln | Pro | Ser | Pro | Asp 255 | Gln |
| Ser | Gly | Leu | Asp 260 | Ile | Asn | Gly | Ile | Lys 265 | Pro | Glu | Pro | Ile | Cys 270 | Asp | Tyr |
| Thr | Pro | Ala 275 | Ser | Gly | Phe | Phe | Pro 280 | Tyr | Cys | Ser | Phe | Thr 285 | Asn | Gly | Glu |
| Thr | Ser 290 | Pro | Thr | Val | Ser | Met 295 | Ala | Glu | Leu | Glu | His 300 | Leu | Ala | Gln | Asn |
| Ile 305 | Ser | Lys | Ser | His | Leu 310 | Glu | Thr | Cys | Gln | Tyr 315 | Leu | Arg | Glu | Glu | Leu 320 |
| Gln | Gln | Ile | Thr | Trp 325 | Gln | Thr | Phe | Leu | Gln 330 | Glu | Glu | Ile | Glu | Asn 335 | Tyr |
| Gln | Asn | Lys | Gln 340 | Arg | Glu | Val | Met | Trp 345 | Gln | Leu | Cys | Ala | Ile 350 | Lys | Ile |
| Thr | Glu | Ala 355 | Ile | Gln | Tyr | Val | Val 360 | Glu | Phe | Ala | Lys | Arg 365 | Ile | Asp | Gly |
| Phe | Met 370 | Glu | Leu | Cys | Gln | Asn 375 | Asp | Gln | Ile | Val | Leu 380 | Leu | Lys | Ala | Gly |
| Ser 385 | Leu | Glu | Val | Val | Phe 390 | Ile | Arg | Met | Cys | Arg 395 | Ala | Phe | Asp | Ser | Gln 400 |
| Asn | Asn | Thr | Val | Tyr 405 | Phe | Asp | Gly | Lys | Tyr 410 | Ala | Ser | Pro | Asp | Val 415 | Phe |
| Lys | Ser | Leu | Gly 420 | Cys | Glu | Asp | Phe | Ile 425 | Ser | Phe | Val | Phe | Glu 430 | Phe | Gly |
| Lys | Ser | Leu | Cys | Ser | Met | His | Leu | Thr | Glu | Asp | Glu | Ile | Ala | Leu | Phe |

|   |   |   |   |   | 435 |   |   |   |   | 440 |   |   |   |   | 445 |   |   |   |
|---|---|---|---|---|---|---|---|---|---|---|---|---|---|---|---|---|---|---|
| Ser | Ala | Phe | Val | Leu | Met | Ser | Ala | Asp | Arg | Ser | Trp | Leu | Gln | Glu | Lys |
|   | 450 |   |   |   |   | 455 |   |   |   |   | 460 |   |   |   |   |
| Val | Lys | Ile | Glu | Lys | Leu | Gln | Gln | Lys | Ile | Gln | Leu | Ala | Leu | Gln | His |
| 465 |   |   |   |   |   | 470 |   |   |   |   | 475 |   |   |   | 480 |
| Val | Leu | Gln | Lys | Asn | His | Arg | Glu | Asp | Gly | Ile | Leu | Thr | Lys | Leu | Ile |
|   |   |   |   | 485 |   |   |   |   | 490 |   |   |   |   | 495 |   |
| Cys | Lys | Val | Ser | Thr | Leu | Arg | Ala | Leu | Cys | Gly | Arg | His | Thr | Glu | Lys |
|   |   |   | 500 |   |   |   |   | 505 |   |   |   | 510 |   |   |   |
| Leu | Met | Ala | Phe | Lys | Ala | Ile | Tyr | Pro | Asp | Ile | Val | Arg | Leu | His | Phe |
|   |   | 515 |   |   |   |   | 520 |   |   |   |   | 525 |   |   |   |
| Pro | Pro | Leu | Tyr | Lys | Glu | Leu | Phe | Thr | Ser | Glu | Phe | Glu | Pro | Ala | Met |
|   | 530 |   |   |   |   | 535 |   |   |   |   | 540 |   |   |   |   |
| Gln | Ile | Asp | Gly |
| 545 |

(2) INFORMATION FOR SEQ ID NO:3:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: AMINO TERMINAL PORTION OF XR1PRIME
        (VERHT3.SEQ)

(ix) FEATURE:
        (A) NAME/KEY: CDS
        (B) LOCATION: 90..386

(xi) SEQUENCE DESCRIPTION: SEQ ID NO:3:

```
CCATCTGTCT GATCACCTTG GACTCCATAG TACACTGGGG CAAAGCACAG CCCCAGTTTC      60

TGGAGGCAGA TGGGTAACCA GGAAAAGGC ATG AAT GAG GGG GCC CCA GGA GAC       113
                                 Met Asn Glu Gly Ala Pro Gly Asp
                                  1               5

AGT GAC TTA GAG ACT GAG GCA AGA GTG CCG TGG TCA ATC ATG GGT CAT       161
Ser Asp Leu Glu Thr Glu Ala Arg Val Pro Trp Ser Ile Met Gly His
        10                  15                  20

TGT CTT CGA ACT GGA CAG GCC AGA ATG TCT GCC ACA CCC ACA CCT GCA       209
Cys Leu Arg Thr Gly Gln Ala Arg Met Ser Ala Thr Pro Thr Pro Ala
 25                  30                  35                  40

GGT GAA GGA GCC AGA AGG GAT GAA CTT TTT GGG ATT CTC CAA ATA CTC       257
Gly Glu Gly Ala Arg Arg Asp Glu Leu Phe Gly Ile Leu Gln Ile Leu
                     45                  50                  55

CAT CAG TGT ATC CTG TCT TCA GGT GAT GCT TTT GTT CTT ACT GGC GTC       305
His Gln Cys Ile Leu Ser Ser Gly Asp Ala Phe Val Leu Thr Gly Val
             60                  65                  70

TGT TGT TCC TGG AGG CAG AAT GGC AAG CCA CCA TAT TCA CAA AAG GAA       353
Cys Cys Ser Trp Arg Gln Asn Gly Lys Pro Pro Tyr Ser Gln Lys Glu
         75                  80                  85

GAT AAG GAA GTA CAA ACT GGA TAC ATG AAT GCT                           386
Asp Lys Glu Val Gln Thr Gly Tyr Met Asn Ala
     90                  95
```

(2) INFORMATION FOR SEQ ID NO:4:

(i) SEQUENCE CHARACTERISTICS:
        (A) LENGTH: 99 amino acids
        (B) TYPE: amino acid ( D ) TOPOLOGY: linear ( i i ) MOLECULE TYPE: protein ( x i ) SEQUENCE DESCRIPTION: SEQ ID NO:4:

| Met | Asn | Glu | Gly | Ala | Pro | Gly | Asp | Ser | Asp | Leu | Glu | Thr | Glu | Ala | Arg |
|---|---|---|---|---|---|---|---|---|---|---|---|---|---|---|---|
| 1 | | | | 5 | | | | | 10 | | | | | 15 | |

| Val | Pro | Trp | Ser | Ile | Met | Gly | His | Cys | Leu | Arg | Thr | Gly | Gln | Ala | Arg |
|---|---|---|---|---|---|---|---|---|---|---|---|---|---|---|---|
| | | | 20 | | | | | 25 | | | | | 30 | | |

| Met | Ser | Ala | Thr | Pro | Thr | Pro | Ala | Gly | Glu | Gly | Ala | Arg | Arg | Asp | Glu |
|---|---|---|---|---|---|---|---|---|---|---|---|---|---|---|---|
| | | 35 | | | | | 40 | | | | | 45 | | | |

| Leu | Phe | Gly | Ile | Leu | Gln | Ile | Leu | His | Gln | Cys | Ile | Leu | Ser | Ser | Gly |
|---|---|---|---|---|---|---|---|---|---|---|---|---|---|---|---|
| | 50 | | | | | 55 | | | | | 60 | | | | |

| Asp | Ala | Phe | Val | Leu | Thr | Gly | Val | Cys | Cys | Ser | Trp | Arg | Gln | Asn | Gly |
|---|---|---|---|---|---|---|---|---|---|---|---|---|---|---|---|
| 65 | | | | | 70 | | | | | 75 | | | | | 80 |

| Lys | Pro | Pro | Tyr | Ser | Gln | Lys | Glu | Asp | Lys | Glu | Val | Gln | Thr | Gly | Tyr |
|---|---|---|---|---|---|---|---|---|---|---|---|---|---|---|---|
| | | | | 85 | | | | | 90 | | | | | 95 | |

Met Asn Ala ( 2 ) INFORMATION FOR SEQ ID NO:5:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: AMINO TERMINAL PORTION OF XR1PRIM2
        ( VERHT5 . SEQ )

( i x ) FEATURE:
        ( A ) NAME/KEY: CDS
        ( B ) LOCATION: 103..300

( x i ) SEQUENCE DESCRIPTION: SEQ ID NO:5:

| GTTTTTTTTT | TTTTTTTGGT | ACCATAGAGT | TGCTCTGAAA | ACAGAAGATA | GAGGGAGTCT | 60 |
|---|---|---|---|---|---|---|

| CGGAGCTCGC | CATCTCCAGC | GATCTCTACA | TTGGGAAAAA | AC ATG GAG TCA GCT | | 114 |
|---|---|---|---|---|---|---|
| | | | | Met Glu Ser Ala | | |
| | | | | 1 | | |

| CCG | GCA | AGG | GAG | ACC | CCG | CTG | AAC | CAG | GAA | TCC | GCC | GCC | CCC | GAC | CCC | 162 |
|---|---|---|---|---|---|---|---|---|---|---|---|---|---|---|---|---|
| Pro | Ala | Arg | Glu | Thr | Pro | Leu | Asn | Gln | Glu | Ser | Ala | Ala | Pro | Asp | Pro | |
| 5 | | | | | 10 | | | | | 15 | | | | | 20 | |

| GCC | GCC | AGC | GAG | CCA | GGC | AGC | AGC | GGC | GCG | GAC | GCG | GCC | GCC | GGC | TCC | 210 |
|---|---|---|---|---|---|---|---|---|---|---|---|---|---|---|---|---|
| Ala | Ala | Ser | Glu | Pro | Gly | Ser | Ser | Gly | Ala | Asp | Ala | Ala | Ala | Gly | Ser | |
| | | | | 25 | | | | | 30 | | | | | 35 | | |

| CGC | AAG | AGC | GAG | CCG | CCT | GCC | CCG | GTG | CGC | AGA | CAG | AGC | TAT | TCC | AGC | 258 |
|---|---|---|---|---|---|---|---|---|---|---|---|---|---|---|---|---|
| Arg | Lys | Ser | Glu | Pro | Pro | Ala | Pro | Val | Arg | Arg | Gln | Ser | Tyr | Ser | Ser | |
| | | | 40 | | | | | 45 | | | | | 50 | | | |

| ACC | AGC | AGA | GGT | ATC | TCA | GTA | ACG | AAG | AAG | ACA | CAT | ACA | TCT | | | 300 |
|---|---|---|---|---|---|---|---|---|---|---|---|---|---|---|---|---|
| Thr | Ser | Arg | Gly | Ile | Ser | Val | Thr | Lys | Lys | Thr | His | Thr | Ser | | | |
| | | 55 | | | | | 60 | | | | | 65 | | | | |

( 2 ) INFORMATION FOR SEQ ID NO:6:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Glu Ser Ala Pro Ala Arg Glu Thr Pro Leu Asn Gln Glu Ser Ala
 1               5                  10                  15

Ala Pro Asp Pro Ala Ala Ser Glu Pro Gly Ser Ser Gly Ala Asp Ala
             20                  25                  30

Ala Ala Gly Ser Arg Lys Ser Glu Pro Pro Ala Pro Val Arg Arg Gln
         35                  40                  45

Ser Tyr Ser Ser Thr Ser Arg Gly Ile Ser Val Thr Lys Lys Thr His
     50                  55                  60

Thr Ser
 65
```

( 2 ) INFORMATION FOR SEQ ID NO:7:

( i ) SEQUENCE CHARACTERISTICS:
        ( A ) LENGTH: 1659 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR2 (XR2.SEG)

( i x ) FEATURE:
        ( A ) NAME/KEY: CDS
        ( B ) LOCATION: 148..1470

( x i ) SEQUENCE DESCRIPTION: SEQ ID NO:7:

```
GATATCCGTG ACATCATTGC CTGAGTCCAC TGCAAAAAGC TGTCCCCAGA GCAGGAGGGC        60

AATGACAGCT CCCAGGGCAC TCATCTTGAC TGCTCTTGCC TGGGGATTTG ACAGTGCCT       120

TGGTAATGAC CAGGGCTCCA GAAAGAG ATG TCC TTG TGG CTG GGG GCC CCT          171
                              Met Ser Leu Trp Leu Gly Ala Pro
                               1               5

GTG CCT GAC ATT CCT CCT GAC TCT GCG GTG GAG CTG TGG AAG CCA GGC        219
Val Pro Asp Ile Pro Pro Asp Ser Ala Val Glu Leu Trp Lys Pro Gly
         10                  15                  20

GCA CAG GAT GCA AGC AGC CAG GCC CAG GGA GGC AGC AGC TGC ATC CTC        267
Ala Gln Asp Ala Ser Ser Gln Ala Gln Gly Gly Ser Ser Cys Ile Leu
 25                  30                  35                  40

AGA GAG GAA GCC AGG ATG CCC CAC TCT GCT GGG GGT ACT GCA GAG CCC        315
Arg Glu Glu Ala Arg Met Pro His Ser Ala Gly Gly Thr Ala Glu Pro
                 45                  50                  55

ACA GCC CTG CTC ACC AGG GCA GAG CCC CCT TCA GAA CCC ACA GAG ATC        363
Thr Ala Leu Leu Thr Arg Ala Glu Pro Pro Ser Glu Pro Thr Glu Ile
             60                  65                  70

CGT CCA CAA AAG CGG AAA AAG GGG CCA GCC CCC AAA ATG CTG GGG AAC        411
Arg Pro Gln Lys Arg Lys Lys Gly Pro Ala Pro Lys Met Leu Gly Asn
         75                  80                  85

GAG CTA TGC AGC GTG TGT GGG GAC AAG GCC TCG GGC TTC CAC TAC AAT        459
Glu Leu Cys Ser Val Cys Gly Asp Lys Ala Ser Gly Phe His Tyr Asn
     90                  95                 100

GTT CTG AGC TGC GAG GGC TGC AAG GGA TTC TTC CGC CGC AGC GTC ATC        507
Val Leu Ser Cys Glu Gly Cys Lys Gly Phe Phe Arg Arg Ser Val Ile
105                 110                 115                 120

AAG GGA GCG CAC TAC ATC TGC CAC AGT GGC GGC CAC TGC CCC ATG GAC        555
Lys Gly Ala His Tyr Ile Cys His Ser Gly Gly His Cys Pro Met Asp
                125                 130                 135

ACC TAC ATG CGT CGC AAG TGC CAG GAG TGT CGG CTT CGC AAA TGC CGT        603
Thr Tyr Met Arg Arg Lys Cys Gln Glu Cys Arg Leu Arg Lys Cys Arg
            140                 145                 150
```

```
CAG GCT GGC ATG CGG GAG GAG TGT GTC CTG TCA GAA GAA CAG ATC CGC    651
Gln Ala Gly Met Arg Glu Glu Cys Val Leu Ser Glu Glu Gln Ile Arg
        155                 160                 165

CTG AAG AAA CTG AAG CGG CAA GAG GAG GAA CAG GCT CAT GCC ACA TCC    699
Leu Lys Lys Leu Lys Arg Gln Glu Glu Glu Gln Ala His Ala Thr Ser
        170                 175                 180

TTG CCC CCC AGG CGT TCC TCA CCC CCC CAA ATC CTG CCC CAG CTC AGC    747
Leu Pro Pro Arg Arg Ser Ser Pro Pro Gln Ile Leu Pro Gln Leu Ser
185                 190                 195                 200

CCG GAA CAA CTG GGC ATG ATC GAG AAG CTC GTC GCT GCC CAG CAA CAG    795
Pro Glu Gln Leu Gly Met Ile Glu Lys Leu Val Ala Ala Gln Gln Gln
                    205                 210                 215

TGT AAC CGG CGC TCC TTT TCT GAC CGG CTT CGA GTC ACG CCT TGG CCC    843
Cys Asn Arg Arg Ser Phe Ser Asp Arg Leu Arg Val Thr Pro Trp Pro
            220                 225                 230

ATG GCA CCA GAT CCC CAT AGC CGG GAG GCC CGT CAG CAG CGC TTT GCC    891
Met Ala Pro Asp Pro His Ser Arg Glu Ala Arg Gln Gln Arg Phe Ala
        235                 240                 245

CAC TTC ACT GAG CTG GCC ATC GTC TCT GTG CAG GAG ATA GTT GAC TTT    939
His Phe Thr Glu Leu Ala Ile Val Ser Val Gln Glu Ile Val Asp Phe
        250                 255                 260

GCT AAA CAG CTA CCC GGC TTC CTG CAG CTC AGC CGG GAG GAC CAG ATT    987
Ala Lys Gln Leu Pro Gly Phe Leu Gln Leu Ser Arg Glu Asp Gln Ile
265                 270                 275                 280

GCC CTG CTG AAG ACC TCT GCG ATC GAG GTG ATG CTT CTG GAG ACA TCT   1035
Ala Leu Leu Lys Thr Ser Ala Ile Glu Val Met Leu Leu Glu Thr Ser
                    285                 290                 295

CGG AGG TAC AAC CCT GGG AGT GAG AGT ATC ACC TTC CTC AAG GAT TTC   1083
Arg Arg Tyr Asn Pro Gly Ser Glu Ser Ile Thr Phe Leu Lys Asp Phe
            300                 305                 310

AGT TAT AAC CGG GAA GAC TTT GCC AAA GCA GGG CTG CAA GTG GAA TTC   1131
Ser Tyr Asn Arg Glu Asp Phe Ala Lys Ala Gly Leu Gln Val Glu Phe
        315                 320                 325

ATC AAC CCC ATC TTC GAG TTC TCC AGG GCC ATG AAT GAG CTG CAA CTC   1179
Ile Asn Pro Ile Phe Glu Phe Ser Arg Ala Met Asn Glu Leu Gln Leu
        330                 335                 340

AAT GAT GCC GAG TTT GCC TTG CTC ATT GCT ATC AGC ATC TTC TCT GCA   1227
Asn Asp Ala Glu Phe Ala Leu Leu Ile Ala Ile Ser Ile Phe Ser Ala
345                 350                 355                 360

GAC CGG CCC AAC GTG CAG GAC CAG CTC CAG GTG GAG AGG CTG CAG CAC   1275
Asp Arg Pro Asn Val Gln Asp Gln Leu Gln Val Glu Arg Leu Gln His
                    365                 370                 375

ACA TAT GTG GAA GCC CTG CAT GCC TAC GTC TCC ATC CAC CAT CCC CAT   1323
Thr Tyr Val Glu Ala Leu His Ala Tyr Val Ser Ile His His Pro His
            380                 385                 390

GAC CGA CTG ATG TTC CCA CGG ATG CTA ATG AAA CTG GTG AGC CTC CGG   1371
Asp Arg Leu Met Phe Pro Arg Met Leu Met Lys Leu Val Ser Leu Arg
        395                 400                 405

ACC CTG AGC AGC GTC CAC TCA GAG CAA GTG TTT GCA CTG CGT CTG CAG   1419
Thr Leu Ser Ser Val His Ser Glu Gln Val Phe Ala Leu Arg Leu Gln
        410                 415                 420

GAC AAA AAG CTC CCA CCG CTG CTC TCT GAG ATC TGG GAT GTG CAC GAA   1467
Asp Lys Lys Leu Pro Pro Leu Leu Ser Glu Ile Trp Asp Val His Glu
425                 430                 435                 440

TGACTGTTCT GTCCCCATAT TTTCTGTTTT CTTGGCCGGA TGGCTGAGGC CTGGTGGCTG    1527

CCTCCTAGAA GTGGAACAGA CTGAGAAGGG CAAACATTCC TGGGAGCTGG GCAAGGAGAT    1587

CCTCCCGTGG CATTAAAAGA GAGTCAAAGG GTAAAAAAAA AAAAAAAAAA AAAAAAAAAA    1647

AAAAAGGAAT TC                                                       1659
```

( 2 ) INFORMATION FOR SEQ ID NO:8:

( i ) SEQUENCE CHARACTERISTICS:
        ( A ) LENGTH: 440 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ser Leu Trp Leu Gly Ala Pro Val Pro Asp Ile Pro Pro Asp Ser
 1               5                  10                  15
Ala Val Glu Leu Trp Lys Pro Gly Ala Gln Asp Ala Ser Ser Gln Ala
            20                  25                  30
Gln Gly Gly Ser Ser Cys Ile Leu Arg Glu Glu Ala Arg Met Pro His
        35                  40                  45
Ser Ala Gly Gly Thr Ala Glu Pro Thr Ala Leu Leu Thr Arg Ala Glu
    50                  55                  60
Pro Pro Ser Glu Pro Thr Glu Ile Arg Pro Gln Lys Arg Lys Lys Gly
65                  70                  75                  80
Pro Ala Pro Lys Met Leu Gly Asn Glu Leu Cys Ser Val Cys Gly Asp
                85                  90                  95
Lys Ala Ser Gly Phe His Tyr Asn Val Leu Ser Cys Glu Gly Cys Lys
            100                 105                 110
Gly Phe Phe Arg Arg Ser Val Ile Lys Gly Ala His Tyr Ile Cys His
        115                 120                 125
Ser Gly Gly His Cys Pro Met Asp Thr Tyr Met Arg Arg Lys Cys Gln
    130                 135                 140
Glu Cys Arg Leu Arg Lys Cys Arg Gln Ala Gly Met Arg Glu Glu Cys
145                 150                 155                 160
Val Leu Ser Glu Glu Gln Ile Arg Leu Lys Lys Leu Lys Arg Gln Glu
                165                 170                 175
Glu Glu Gln Ala His Ala Thr Ser Leu Pro Pro Arg Arg Ser Ser Pro
            180                 185                 190
Pro Gln Ile Leu Pro Gln Leu Ser Pro Glu Gln Leu Gly Met Ile Glu
        195                 200                 205
Lys Leu Val Ala Ala Gln Gln Gln Cys Asn Arg Arg Ser Phe Ser Asp
    210                 215                 220
Arg Leu Arg Val Thr Pro Trp Pro Met Ala Pro Asp Pro His Ser Arg
225                 230                 235                 240
Glu Ala Arg Gln Gln Arg Phe Ala His Phe Thr Glu Leu Ala Ile Val
                245                 250                 255
Ser Val Gln Glu Ile Val Asp Phe Ala Lys Gln Leu Pro Gly Phe Leu
            260                 265                 270
Gln Leu Ser Arg Glu Asp Gln Ile Ala Leu Leu Lys Thr Ser Ala Ile
        275                 280                 285
Glu Val Met Leu Leu Glu Thr Ser Arg Arg Tyr Asn Pro Gly Ser Glu
    290                 295                 300
Ser Ile Thr Phe Leu Lys Asp Phe Ser Tyr Asn Arg Glu Asp Phe Ala
305                 310                 315                 320
Lys Ala Gly Leu Gln Val Glu Phe Ile Asn Pro Ile Phe Glu Phe Ser
                325                 330                 335
Arg Ala Met Asn Glu Leu Gln Leu Asn Asp Ala Glu Phe Ala Leu Leu
            340                 345                 350
Ile Ala Ile Ser Ile Phe Ser Ala Asp Arg Pro Asn Val Gln Asp Gln
        355                 360                 365
```

| | | | | | | | | | | | | | | |
|---|---|---|---|---|---|---|---|---|---|---|---|---|---|---|
| Leu | Gln | Val | Glu | Arg | Leu | Gln | His | Thr | Tyr | Val | Glu | Ala | Leu | His | Ala |
| | 370 | | | | | 375 | | | | | 380 | | | | |
| Tyr | Val | Ser | Ile | His | His | Pro | His | Asp | Arg | Leu | Met | Phe | Pro | Arg | Met |
| 385 | | | | | 390 | | | | | 395 | | | | | 400 |
| Leu | Met | Lys | Leu | Val | Ser | Leu | Arg | Thr | Leu | Ser | Ser | Val | His | Ser | Glu |
| | | | | 405 | | | | | 410 | | | | | 415 | |
| Gln | Val | Phe | Ala | Leu | Arg | Leu | Gln | Asp | Lys | Lys | Leu | Pro | Pro | Leu | Leu |
| | | | 420 | | | | | 425 | | | | | 430 | | |
| Ser | Glu | Ile | Trp | Asp | Val | His | Glu |
| | | 435 | | | | | 440 |

( 2 ) INFORMATION FOR SEQ ID NO:9:

( i ) SEQUENCE CHARACTERISTICS:
( A ) LENGTH: 2009 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( B ) CLONE: XR4 (XR4.SEG)

( i x ) FEATURE:
( A ) NAME/KEY: CDS
( B ) LOCATION: 263..1582

( x i ) SEQUENCE DESCRIPTION: SEQ ID NO:9:

```
GAATTCCCTG GGGATTAATG GGAAAAGTTT TGGCAGGAGC TGGGGGATTC TGCGGAGCCT         60

GCGGGACGGC GGCAGCGGCG CGAGAGGCGG CCGGGACAGT GCTGTGCAGC GGTGTGGGTA        120

TGCGCATGGG ACTCACTCAG AGGCTCCTGC TCACTGACAG ATGAAGACAA ACCCACGGTA        180

AAGGCAGTCC ATCTGCGCTC AGACCCAGAT GGTGGCAGAG CTATGACCAG GCCTGCAGCG        240

CCACGCCAAG TGGGGGTCAG TC ATG GAA CAG CCA CAG GAG GAG ACC CCT GAG        292
              Met Glu Gln Pro Gln Glu Glu Thr Pro Glu
                1               5                  10

GCC CGG GAA GAG GAG AAA GAG GAA GTG GCC ATG GGT GAC GGA GCC CCG        340
Ala Arg Glu Glu Glu Lys Glu Glu Val Ala Met Gly Asp Gly Ala Pro
                  15               20                25

GAG CTC AAT GGG GGA CCA GAA CAC ACG CTT CCT TCC AGC AGC TGT GCA        388
Glu Leu Asn Gly Gly Pro Glu His Thr Leu Pro Ser Ser Ser Cys Ala
          30                   35              40

GAC CTC TCC CAG AAT TCC TCC CCT TCC TCC CTG CTG GAC CAG CTG CAG        436
Asp Leu Ser Gln Asn Ser Ser Pro Ser Ser Leu Leu Asp Gln Leu Gln
         45                   50                 55

ATG GGC TGT GAT GGG GCC TCA GGC GGC AGC CTC AAC ATG GAA TGT CGG        484
Met Gly Cys Asp Gly Ala Ser Gly Gly Ser Leu Asn Met Glu Cys Arg
     60                  65                 70

GTG TGC GGG GAC AAG GCC TCG GGC TTC CAC TAC GGG GTC CAC GCG TGC        532
Val Cys Gly Asp Lys Ala Ser Gly Phe His Tyr Gly Val His Ala Cys
 75                  80                  85                  90

GAG GGG TGC AAG GGC TTC TTC CGC CGG ACA ATC CGC ATG AAG CTC GAG        580
Glu Gly Cys Lys Gly Phe Phe Arg Arg Thr Ile Arg Met Lys Leu Glu
                  95              100               105

TAT GAG AAG TGC GAT CGG ATC TGC AAG ATC CAG AAG AAG AAC CGC AAC        628
Tyr Glu Lys Cys Asp Arg Ile Cys Lys Ile Gln Lys Lys Asn Arg Asn
              110                 115               120

AAG TGT CAG TAC TGC CGC TTC CAG AAG TGC CTG GCA CTC GGC ATG TCG        676
Lys Cys Gln Tyr Cys Arg Phe Gln Lys Cys Leu Ala Leu Gly Met Ser
         125                130                135
```

```
CAC AAC GCT ATC CGC TTT GGA CGG ATG CCG GAC GGC GAG AAG AGG AAG     724
His Asn Ala Ile Arg Phe Gly Arg Met Pro Asp Gly Glu Lys Arg Lys
        140                 145                 150

CTG GTG GCG GGG CTG ACT GCC AGC GAG GGG TGC CAG CAC AAC CCC CAG     772
Leu Val Ala Gly Leu Thr Ala Ser Glu Gly Cys Gln His Asn Pro Gln
155                 160                 165                 170

CTG GCC GAC CTG AAG GCC TTC TCT AAG CAC ATC TAC AAC GCC TAC CTG     820
Leu Ala Asp Leu Lys Ala Phe Ser Lys His Ile Tyr Asn Ala Tyr Leu
                175                 180                 185

AAA AAC TTC AAC ATG ACC AAA AAG AAG GCC CGG AGC ATC CTC ACC GGC     868
Lys Asn Phe Asn Met Thr Lys Lys Lys Ala Arg Ser Ile Leu Thr Gly
                    190                 195                 200

AAG TCC AGC CAC AAC GCA CCC TTT GTC ATC CAC GAC ATC GAG ACA CTG     916
Lys Ser Ser His Asn Ala Pro Phe Val Ile His Asp Ile Glu Thr Leu
        205                 210                 215

TGG CAG GCA GAG AAG GGC CTG GTG TGG AAA CAG CTG GTG AAC GTG CCG     964
Trp Gln Ala Glu Lys Gly Leu Val Trp Lys Gln Leu Val Asn Val Pro
220                 225                 230

CCC TAC AAC GAG ATC AGT GTG CAC GTG TTC TAC CGC TGC CAG TCC ACC    1012
Pro Tyr Asn Glu Ile Ser Val His Val Phe Tyr Arg Cys Gln Ser Thr
235                 240                 245                 250

ACA GTG GAG ACA GTC CGA GAG CTC ACC GAG TTC GCC AAG AAC ATC CCC    1060
Thr Val Glu Thr Val Arg Glu Leu Thr Glu Phe Ala Lys Asn Ile Pro
                255                 260                 265

AAC TTC AGC AGC CTC TTC CTC AAT GAC CAG GTG ACC CTC CTC AAG TAT    1108
Asn Phe Ser Ser Leu Phe Leu Asn Asp Gln Val Thr Leu Leu Lys Tyr
                270                 275                 280

GGC GTG CAC GAG GCC ATC TTT GCC ATG CTG GCC TCC ATC GTC AAC AAA    1156
Gly Val His Glu Ala Ile Phe Ala Met Leu Ala Ser Ile Val Asn Lys
        285                 290                 295

GAC GGG CTG CTG GTG GCC AAC GGC AGT GGC TTC GTC ACC CAC GAG TTC    1204
Asp Gly Leu Leu Val Ala Asn Gly Ser Gly Phe Val Thr His Glu Phe
300                 305                 310

TTG CGA AGT CTC CGC AAG CCC TTC AGT GAC ATC ATT GAG CCC AAG TTC    1252
Leu Arg Ser Leu Arg Lys Pro Phe Ser Asp Ile Ile Glu Pro Lys Phe
315                 320                 325                 330

GAG TTT GCT GTC AAG TTC AAT GCG CTG GAG CTC GAT GAC AGT GAC CTG    1300
Glu Phe Ala Val Lys Phe Asn Ala Leu Glu Leu Asp Asp Ser Asp Leu
                335                 340                 345

GCG CTC TTC ATC GCG GCC ATC ATT CTG TGT GGA GAC CGG CCA GGC CTC    1348
Ala Leu Phe Ile Ala Ala Ile Ile Leu Cys Gly Asp Arg Pro Gly Leu
                350                 355                 360

ATG AAT GTG CCC CAG GTA GAA GCC ATC CAG GAC ACC ATT CTG CGG GCT    1396
Met Asn Val Pro Gln Val Glu Ala Ile Gln Asp Thr Ile Leu Arg Ala
        365                 370                 375

CTA GAA TTC CAT CTG CAG GTC AAC CAC CCT GAC AGC CAG TAC CTC TTC    1444
Leu Glu Phe His Leu Gln Val Asn His Pro Asp Ser Gln Tyr Leu Phe
380                 385                 390

CCC AAG CTG CTG CAG AAG ATG GCA GAC CTG CGG CAC GTG GTC ACT GAG    1492
Pro Lys Leu Leu Gln Lys Met Ala Asp Leu Arg His Val Val Thr Glu
395                 400                 405                 410

CAT GCC CAG ATG ATG CAG TGG CTA AAG AAG ACG GAG AGT GAG ACC TTG    1540
His Ala Gln Met Met Gln Trp Leu Lys Lys Thr Glu Ser Glu Thr Leu
                415                 420                 425

CTG CAC CCC CTG CTC CAG GAA ATC TAC AAG GAC ATG TAC TAAGGCCGCA    1589
Leu His Pro Leu Leu Gln Glu Ile Tyr Lys Asp Met Tyr
        430                 435                 440

GCCCAGGCCT CCCCTCAGGC TCTGCTGGGC CCAGCCACGG ACTGTTCAGA GGACCAGCCA    1649

CAGGCACTGG CAGTCAAGCA GCTAGAGCCT ACTCACAACA CTCCAGACAC GTGGCCCAGA    1709
```

```
CTCTTCCCCC  AACACCCCCA  CCCCCACCAA  CCCCCCCATT  CCCCCAACCC  CCCTCCCCCA    1769

CCCCGCTCTC  CCCATGGCCC  GTTTCCTGTT  TCTCCTCAGC  ACCTCCTGTT  CTTGCTGTCT    1829

CCCTAGCGCC  CTTGCTCCCC  CCCCTTTGCC  TTCCTTCTCT  AGCATCCCCC  TCCTCCCAGT    1889

CCTCACATTT  GTCTGATTCA  CAGCAGACAG  CCCGTTGGTA  CGCTCACCAG  CAGCCTAAAA    1949

GCAGTGGGCC  TGTGCTGGCC  CAGTCCTGCC  TCTCCTCTCT  ATCCCCTTCA  AAGGGAATTC    2009
```

( 2 ) INFORMATION FOR SEQ ID NO:10:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Gln Pro Gln Glu Glu Thr Pro Glu Ala Arg Glu Glu Lys
 1               5                  10                  15

Glu Glu Val Ala Met Gly Asp Gly Ala Pro Glu Leu Asn Gly Gly Pro
             20                  25                  30

Glu His Thr Leu Pro Ser Ser Ser Cys Ala Asp Leu Ser Gln Asn Ser
         35                  40                  45

Ser Pro Ser Ser Leu Leu Asp Gln Leu Gln Met Gly Cys Asp Gly Ala
     50                  55                  60

Ser Gly Gly Ser Leu Asn Met Glu Cys Arg Val Cys Gly Asp Lys Ala
65                  70                  75                  80

Ser Gly Phe His Tyr Gly Val His Ala Cys Glu Gly Cys Lys Gly Phe
                 85                  90                  95

Phe Arg Arg Thr Ile Arg Met Lys Leu Glu Tyr Glu Lys Cys Asp Arg
                100                 105                 110

Ile Cys Lys Ile Gln Lys Lys Asn Arg Asn Lys Cys Gln Tyr Cys Arg
             115                 120                 125

Phe Gln Lys Cys Leu Ala Leu Gly Met Ser His Asn Ala Ile Arg Phe
         130                 135                 140

Gly Arg Met Pro Asp Gly Glu Lys Arg Lys Leu Val Ala Gly Leu Thr
145                 150                 155                 160

Ala Ser Glu Gly Cys Gln His Asn Pro Gln Leu Ala Asp Leu Lys Ala
                165                 170                 175

Phe Ser Lys His Ile Tyr Asn Ala Tyr Leu Lys Asn Phe Asn Met Thr
            180                 185                 190

Lys Lys Lys Ala Arg Ser Ile Leu Thr Gly Lys Ser Ser His Asn Ala
        195                 200                 205

Pro Phe Val Ile His Asp Ile Glu Thr Leu Trp Gln Ala Glu Lys Gly
    210                 215                 220

Leu Val Trp Lys Gln Leu Val Asn Val Pro Pro Tyr Asn Glu Ile Ser
225                 230                 235                 240

Val His Val Phe Tyr Arg Cys Gln Ser Thr Thr Val Glu Thr Val Arg
                245                 250                 255

Glu Leu Thr Glu Phe Ala Lys Asn Ile Pro Asn Phe Ser Ser Leu Phe
            260                 265                 270

Leu Asn Asp Gln Val Thr Leu Leu Lys Tyr Gly Val His Glu Ala Ile
        275                 280                 285

Phe Ala Met Leu Ala Ser Ile Val Asn Lys Asp Gly Leu Leu Val Ala
    290                 295                 300

Asn Gly Ser Gly Phe Val Thr His Glu Phe Leu Arg Ser Leu Arg Lys
```

```
305                     310                    315                    320
Pro  Phe  Ser  Asp  Ile  Ile  Glu  Pro  Lys  Phe  Glu  Phe  Ala  Val  Lys  Phe
                         325                    330                    335

Asn  Ala  Leu  Glu  Leu  Asp  Asp  Ser  Asp  Leu  Ala  Leu  Phe  Ile  Ala  Ala
               340                    345                    350

Ile  Ile  Leu  Cys  Gly  Asp  Arg  Pro  Gly  Leu  Met  Asn  Val  Pro  Gln  Val
               355                    360                    365

Glu  Ala  Ile  Gln  Asp  Thr  Ile  Leu  Arg  Ala  Leu  Glu  Phe  His  Leu  Gln
          370                    375                    380

Val  Asn  His  Pro  Asp  Ser  Gln  Tyr  Leu  Phe  Pro  Lys  Leu  Leu  Gln  Lys
385                     390                    395                         400

Met  Ala  Asp  Leu  Arg  His  Val  Val  Thr  Glu  His  Ala  Gln  Met  Met  Gln
                    405                    410                    415

Trp  Leu  Lys  Lys  Thr  Glu  Ser  Glu  Thr  Leu  Leu  His  Pro  Leu  Leu  Gln
               420                    425                    430

Glu  Ile  Tyr  Lys  Asp  Met  Tyr
               435
```

( 2 ) INFORMATION FOR SEQ ID NO:11:

( i ) SEQUENCE CHARACTERISTICS:
        ( A ) LENGTH: 2468 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR5 (XR5.SEQ)

( i x ) FEATURE:
        ( A ) NAME/KEY: CDS
        ( B ) LOCATION: 1..1677

( x i ) SEQUENCE DESCRIPTION: SEQ ID NO:11:

```
GAA  TTC  CGG  CGC  GGA  GGG  GCG  CGG  CGC  GAG  GGG  CCG  GAG  CCG  GGC  GGC      48
Glu  Phe  Arg  Arg  Gly  Gly  Ala  Arg  Arg  Glu  Gly  Pro  Glu  Pro  Gly  Gly
  1                    5                     10                    15

TCA  GGG  GCC  CAG  AGA  GTG  CGG  CGG  CCG  AGA  GCC  TGC  CGG  CCC  CTG  ACA      96
Ser  Gly  Ala  Gln  Arg  Val  Arg  Arg  Pro  Arg  Ala  Cys  Arg  Pro  Leu  Thr
                20                     25                     30

GCC  CCC  TCC  CCC  CGT  GGA  AGA  CCA  GGA  CGA  CGA  CTA  CGA  AGG  CGC  AAG     144
Ala  Pro  Ser  Pro  Arg  Gly  Arg  Pro  Gly  Arg  Arg  Leu  Arg  Arg  Arg  Lys
          35                     40                     45

TCA  TGG  CGG  AGC  AGC  GAA  CGC  CGA  GAG  GGC  CCT  GAG  CAC  CGC  CGC  ATG     192
Ser  Trp  Arg  Ser  Ser  Glu  Arg  Arg  Glu  Gly  Pro  Glu  His  Arg  Arg  Met
    50                     55                     60

GAG  CGG  GAC  GAA  CGG  CCA  CCT  AGC  GGA  GGG  GGA  GGC  GGG  GGC  GGC  TCG     240
Glu  Arg  Asp  Glu  Arg  Pro  Pro  Ser  Gly  Gly  Gly  Gly  Gly  Gly  Gly  Ser
 65                     70                     75                     80

GCG  GGG  TTC  CTG  GAG  CCG  CCC  GCC  GCG  CTC  CCT  CCG  CCG  CCG  CGC  AAC     288
Ala  Gly  Phe  Leu  Glu  Pro  Pro  Ala  Ala  Leu  Pro  Pro  Pro  Pro  Arg  Asn
                    85                     90                     95

GGT  TTC  TGT  CAG  GAT  GAA  TTG  GCA  GAG  CTT  GAT  CCA  GGC  ACT  AAT  GGA     336
Gly  Phe  Cys  Gln  Asp  Glu  Leu  Ala  Glu  Leu  Asp  Pro  Gly  Thr  Asn  Gly
              100                    105                    110

GAG  ACT  GAC  AGT  TTA  ACA  CTT  GGC  CAA  GGC  CAT  ATA  CCT  GTT  TCC  GTC     384
Glu  Thr  Asp  Ser  Leu  Thr  Leu  Gly  Gln  Gly  His  Ile  Pro  Val  Ser  Val
         115                    120                    125

CCA  GAT  GAT  CGA  GCT  GAA  CAA  CGA  ACC  TGT  CTC  ATC  TGT  GGG  GAC  CGC     432
Pro  Asp  Asp  Arg  Ala  Glu  Gln  Arg  Thr  Cys  Leu  Ile  Cys  Gly  Asp  Arg
```

```
                    130                        135                         140
GCT  ACG  GGC  TTG  CAC  TAT  GGG  ATC  ATC  TCC  TGC  GAG  GGC  TGC  AAG  GGG          480
Ala  Thr  Gly  Leu  His  Tyr  Gly  Ile  Ile  Ser  Cys  Glu  Gly  Cys  Lys  Gly
145                      150                      155                      160

TTT  TTC  AAG  AGG  AGC  ATT  TGC  AAC  AAA  CGG  GTG  TAT  CGG  TGC  AGT  CGT          528
Phe  Phe  Lys  Arg  Ser  Ile  Cys  Asn  Lys  Arg  Val  Tyr  Arg  Cys  Ser  Arg
                    165                      170                      175

GAC  AAG  AAC  TGT  GTC  ATG  TCC  CGG  AAG  CAG  AGG  AAC  AGA  TGT  CAG  TAC          576
Asp  Lys  Asn  Cys  Val  Met  Ser  Arg  Lys  Gln  Arg  Asn  Arg  Cys  Gln  Tyr
               180                      185                      190

TGC  CGC  CTG  CTC  AAG  TGT  CTC  CAG  ATG  GGC  ATG  AAC  AGG  AAG  GCT  ATC          624
Cys  Arg  Leu  Leu  Lys  Cys  Leu  Gln  Met  Gly  Met  Asn  Arg  Lys  Ala  Ile
          195                      200                      205

AGA  GAA  GAT  GGC  ATG  CCT  GGA  GGC  CGG  AAC  AAG  AGC  ATT  GGA  CCA  GTC          672
Arg  Glu  Asp  Gly  Met  Pro  Gly  Gly  Arg  Asn  Lys  Ser  Ile  Gly  Pro  Val
210                      215                      220

CAG  ATA  TCA  GAA  GAA  GAA  ATT  GAA  AGA  ATC  ATG  TCT  GGA  CAG  GAG  TTT          720
Gln  Ile  Ser  Glu  Glu  Glu  Ile  Glu  Arg  Ile  Met  Ser  Gly  Gln  Glu  Phe
225                      230                      235                      240

GAG  GAA  GAA  GCC  AAT  CAC  TGG  AGC  AAC  CAT  GGT  GAC  AGC  GAC  CAC  AGT          768
Glu  Glu  Glu  Ala  Asn  His  Trp  Ser  Asn  His  Gly  Asp  Ser  Asp  His  Ser
                    245                      250                      255

TCC  CCT  GGG  AAC  AGG  GCT  TCA  GAG  AGC  AAC  CAG  CCC  TCA  CCA  GGC  TCC          816
Ser  Pro  Gly  Asn  Arg  Ala  Ser  Glu  Ser  Asn  Gln  Pro  Ser  Pro  Gly  Ser
               260                      265                      270

ACA  CTA  TCA  TCC  AGT  AGG  TCT  GTG  GAA  CTA  AAT  GGA  TTC  ATG  GCA  TTC          864
Thr  Leu  Ser  Ser  Ser  Arg  Ser  Val  Glu  Leu  Asn  Gly  Phe  Met  Ala  Phe
          275                      280                      285

AGG  GAT  CAG  TAC  ATG  GGG  ATG  TCA  GTG  CCT  CCA  CAT  TAT  CAA  TAC  ATA          912
Arg  Asp  Gln  Tyr  Met  Gly  Met  Ser  Val  Pro  Pro  His  Tyr  Gln  Tyr  Ile
290                      295                      300

CCA  CAC  CTT  TTT  AGC  TAT  TCT  GGC  CAC  TCA  CCA  CTT  TTG  CCC  CCA  CAA          960
Pro  His  Leu  Phe  Ser  Tyr  Ser  Gly  His  Ser  Pro  Leu  Leu  Pro  Pro  Gln
305                      310                      315                      320

GCT  CGA  AGC  CTG  GAC  CCT  CAG  TCC  TAC  AGT  CTG  ATT  CAT  CAG  CTG  ATG         1008
Ala  Arg  Ser  Leu  Asp  Pro  Gln  Ser  Tyr  Ser  Leu  Ile  His  Gln  Leu  Met
                    325                      330                      335

TCA  GCC  GAA  GAC  CTG  GAG  CCA  TTG  GGC  ACA  CCT  ATG  TTG  ATT  GAA  GAT         1056
Ser  Ala  Glu  Asp  Leu  Glu  Pro  Leu  Gly  Thr  Pro  Met  Leu  Ile  Glu  Asp
               340                      345                      350

GGG  TAT  GCT  GTG  ACA  CAG  GCA  GAA  CTG  TTT  GCT  CTG  CTT  TGC  CGC  CTG         1104
Gly  Tyr  Ala  Val  Thr  Gln  Ala  Glu  Leu  Phe  Ala  Leu  Leu  Cys  Arg  Leu
          355                      360                      365

GCC  GAC  GAG  TTG  CTC  TTT  AGG  CAG  ATT  GCC  TGG  ATC  AAG  AAG  CTG  CCT         1152
Ala  Asp  Glu  Leu  Leu  Phe  Arg  Gln  Ile  Ala  Trp  Ile  Lys  Lys  Leu  Pro
370                      375                      380

TTC  TTC  TGC  GAG  CTC  TCA  ATC  AAG  GAT  TAC  ACG  TGC  CTC  TTG  AGC  TCT         1200
Phe  Phe  Cys  Glu  Leu  Ser  Ile  Lys  Asp  Tyr  Thr  Cys  Leu  Leu  Ser  Ser
385                      390                      395                      400

ACG  TGG  CAG  GAG  TTA  ATC  CTG  CTC  TCC  TCC  CTC  ACA  GTG  TAC  AGC  AAG         1248
Thr  Trp  Gln  Glu  Leu  Ile  Leu  Leu  Ser  Ser  Leu  Thr  Val  Tyr  Ser  Lys
                    405                      410                      415

CAG  ATC  TTT  GGG  GAG  CTG  GCT  GAT  GTC  ACA  GCC  AAG  TAC  TCA  CCC  TCT         1296
Gln  Ile  Phe  Gly  Glu  Leu  Ala  Asp  Val  Thr  Ala  Lys  Tyr  Ser  Pro  Ser
               420                      425                      430

GAT  GAA  GAA  CTC  CAC  AGA  TTT  AGT  GAT  GAA  GGG  ATG  GAG  GTG  ATT  GAA         1344
Asp  Glu  Glu  Leu  His  Arg  Phe  Ser  Asp  Glu  Gly  Met  Glu  Val  Ile  Glu
          435                      440                      445

CGA  CTC  ATC  TAC  CTA  TAT  CAC  AAG  TTC  CAT  CAG  CTG  AAG  GTC  AGC  AAC         1392
Arg  Leu  Ile  Tyr  Leu  Tyr  His  Lys  Phe  His  Gln  Leu  Lys  Val  Ser  Asn
```

```
                450                         455                         460
GAG GAG TAC GCA TGC ATG AAA GCA ATT AAC TTC CTG AAT CAA GAT ATC        1440
Glu Glu Tyr Ala Cys Met Lys Ala Ile Asn Phe Leu Asn Gln Asp Ile
465                 470                 475                 480

AGG GGT CTG ACC AGT GCC TCA CAG CTG GAA CAA CTG AAC AAG CGG TAT        1488
Arg Gly Leu Thr Ser Ala Ser Gln Leu Glu Gln Leu Asn Lys Arg Tyr
                485                 490                 495

TGG TAC ATT TGT CAG GAT TTC ACT GAA TAT AAA TAC ACA CAT CAG CCA        1536
Trp Tyr Ile Cys Gln Asp Phe Thr Glu Tyr Lys Tyr Thr His Gln Pro
            500                 505                 510

AAC CGC TTT CCT GAT CTT ATG ATG TGC TTG CCA GAG ATC CGA TAC ATC        1584
Asn Arg Phe Pro Asp Leu Met Met Cys Leu Pro Glu Ile Arg Tyr Ile
        515                 520                 525

GCA GGC AAG ATG GTG AAT GTG CCC CTG GAG CAG CTG CCC CTC CTC TTT        1632
Ala Gly Lys Met Val Asn Val Pro Leu Glu Gln Leu Pro Leu Leu Phe
    530                 535                 540

AAG GTG GTG CTG CAC TCC TGC AAG ACA AGT ACG GTG AAG GAG TGACCTGTGC    1684
Lys Val Val Leu His Ser Cys Lys Thr Ser Thr Val Lys Glu
545                 550                 555

CCTGCACCTC CTTGGGCCAC CCACAGTGCC TTGGGTAGGC AGCACAGGCT CCAGAGGAAA    1744
GAGCCAGAGA CCAAGATGGA GACTGTGGAG CAGCTACCTC CATCACAAGA AGAATTTGTT    1804
TGTTTGTCTG TTTTTAACCT CATTTTTCTA TATATTTATT TCACGACAGA GTTGAATGTA    1864
TGGCCTTCAA CATGATGCAC ATGCTTTTGT GTGAATGCAG CAGATGCATT TCCTTGCAGT    1924
TTACAGAATG TGAAGATGTT TAATGTTACC GTGTTGTCAT TGTTTAGAGA TAGGTTTTTT    1984
TGTATTTTGA TGGAGAGGGT AGGATGGACT AGATGAGTAT TTCCATAATG TTGACAAAGA    2044
CAACTACCTC AATGGAAACA GGTGTATGAC CATCCCTACC TTTTTCCACA TTTTCTCAGC    2104
AGATACACAC TTGTCTGTTA GAGAGCAAAC TGCCTTTTTT ATAGCCACAG ACTTCTAAGT    2164
AAAAGAAGCA AACAAAGGAG CGAAGTGGTA TAGGGAGATT TACTAATGGC CAGTTGGGAC    2224
ATCTGAGAGG CAATTTGATT TTGATCATCT CATCCCACAA GCCTGAAGGC AGAAACTCTG    2284
CCTTACCTTC TGCTGCACCC CTCCCCCCCC CCACACGCTG TTGTCTGTTG ATGCTGCTGT    2344
CAAGTTTTCA TCCAGGTAGA GTCCTAACAA TAAGCCAGTA TGTAGGACTT GCCTCCAGC    2404
GCCCTTGTAG CTCATAGCTG CCTAGTTTGC TGTTCTAGAT CTACCAAGGC CTACTTCGGA    2464
ATTC                                                                  2468
```

( 2 ) INFORMATION FOR SEQ ID NO:12:

( i ) SEQUENCE CHARACTERISTICS:
        ( A ) LENGTH: 558 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Glu Phe Arg Arg Gly Gly Ala Arg Arg Glu Gly Pro Glu Pro Gly Gly
1               5                   10                  15

Ser Gly Ala Gln Arg Val Arg Arg Pro Arg Ala Cys Arg Pro Leu Thr
                20                  25                  30

Ala Pro Ser Pro Arg Gly Arg Pro Gly Arg Arg Leu Arg Arg Arg Lys
            35                  40                  45

Ser Trp Arg Ser Ser Glu Arg Glu Gly Pro Glu His Arg Arg Met
        50                  55                  60

Glu Arg Asp Glu Arg Pro Pro Ser Gly Gly Gly Gly Gly Gly Ser
65              70                  75                  80
```

| | | | | | | | | | | | | | | |
|---|---|---|---|---|---|---|---|---|---|---|---|---|---|---|
| Ala | Gly | Phe | Leu | Glu 85 | Pro | Pro | Ala | Ala 90 | Leu | Pro | Pro | Pro | Arg 95 | Asn |
| Gly | Phe | Cys | Gln 100 | Asp | Glu | Leu | Ala | Glu 105 | Leu | Asp | Pro | Gly | Thr 110 | Asn | Gly |
| Glu | Thr | Asp 115 | Ser | Leu | Thr | Leu | Gly 120 | Gln | Gly | His | Ile | Pro 125 | Val | Ser | Val |
| Pro | Asp 130 | Asp | Arg | Ala | Glu | Gln 135 | Arg | Thr | Cys | Leu | Ile 140 | Cys | Gly | Asp | Arg |
| Ala 145 | Thr | Gly | Leu | His | Tyr 150 | Gly | Ile | Ile | Ser | Cys 155 | Glu | Gly | Cys | Lys | Gly 160 |
| Phe | Phe | Lys | Arg | Ser 165 | Ile | Cys | Asn | Lys | Arg 170 | Val | Tyr | Arg | Cys | Ser 175 | Arg |
| Asp | Lys | Asn | Cys 180 | Val | Met | Ser | Arg | Lys 185 | Gln | Arg | Asn | Arg | Cys 190 | Gln | Tyr |
| Cys | Arg | Leu 195 | Leu | Lys | Cys | Leu | Gln 200 | Met | Gly | Met | Asn | Arg 205 | Lys | Ala | Ile |
| Arg | Glu 210 | Asp | Gly | Met | Pro | Gly 215 | Gly | Arg | Asn | Lys | Ser 220 | Ile | Gly | Pro | Val |
| Gln 225 | Ile | Ser | Glu | Glu | Glu 230 | Ile | Glu | Arg | Ile | Met 235 | Ser | Gly | Gln | Glu | Phe 240 |
| Glu | Glu | Glu | Ala | Asn 245 | His | Trp | Ser | Asn | His 250 | Gly | Asp | Ser | Asp | His 255 | Ser |
| Ser | Pro | Gly | Asn 260 | Arg | Ala | Ser | Glu | Ser 265 | Asn | Gln | Pro | Ser | Pro 270 | Gly | Ser |
| Thr | Leu | Ser 275 | Ser | Ser | Arg | Ser | Val 280 | Glu | Leu | Asn | Gly | Phe 285 | Met | Ala | Phe |
| Arg | Asp 290 | Gln | Tyr | Met | Gly | Met 295 | Ser | Val | Pro | Pro | His 300 | Tyr | Gln | Tyr | Ile |
| Pro 305 | His | Leu | Phe | Ser | Tyr 310 | Ser | Gly | His | Ser | Pro 315 | Leu | Leu | Pro | Pro | Gln 320 |
| Ala | Arg | Ser | Leu | Asp 325 | Pro | Gln | Ser | Tyr | Ser 330 | Leu | Ile | His | Gln | Leu 335 | Met |
| Ser | Ala | Glu | Asp 340 | Leu | Glu | Pro | Leu | Gly 345 | Thr | Pro | Met | Leu | Ile 350 | Glu | Asp |
| Gly | Tyr | Ala 355 | Val | Thr | Gln | Ala | Glu 360 | Leu | Phe | Ala | Leu | Leu 365 | Cys | Arg | Leu |
| Ala | Asp 370 | Glu | Leu | Leu | Phe | Arg 375 | Gln | Ile | Ala | Trp | Ile 380 | Lys | Lys | Leu | Pro |
| Phe 385 | Phe | Cys | Glu | Leu | Ser 390 | Ile | Lys | Asp | Tyr | Thr 395 | Cys | Leu | Leu | Ser | Ser 400 |
| Thr | Trp | Gln | Glu | Leu 405 | Ile | Leu | Leu | Ser | Ser 410 | Leu | Thr | Val | Tyr | Ser 415 | Lys |
| Gln | Ile | Phe | Gly 420 | Glu | Leu | Ala | Asp | Val 425 | Thr | Ala | Lys | Tyr | Ser 430 | Pro | Ser |
| Asp | Glu | Glu | Leu | His 435 | Arg | Phe | Ser | Asp | Glu 440 | Gly | Met | Glu | Val | Ile 445 | Glu |
| Arg | Leu 450 | Ile | Tyr | Leu | Tyr | His 455 | Lys | Phe | His | Gln | Leu 460 | Lys | Val | Ser | Asn |
| Glu 465 | Glu | Tyr | Ala | Cys | Met 470 | Lys | Ala | Ile | Asn | Phe 475 | Leu | Asn | Gln | Asp | Ile 480 |
| Arg | Gly | Leu | Thr | Ser 485 | Ala | Ser | Gln | Leu | Glu 490 | Gln | Leu | Asn | Lys | Arg 495 | Tyr |
| Trp | Tyr | Ile | Cys | Gln | Asp | Phe | Thr | Glu | Tyr | Lys | Tyr | Thr | His | Gln | Pro |

-continued

```
                        500                              505                              510
Asn  Arg  Phe  Pro  Asp  Leu  Met  Met  Cys  Leu  Pro  Glu  Ile  Arg  Tyr  Ile
              515                      520                          525

Ala  Gly  Lys  Met  Val  Asn  Val  Pro  Leu  Glu  Gln  Leu  Pro  Leu  Leu  Phe
              530                      535                          540

Lys  Val  Val  Leu  His  Ser  Cys  Lys  Thr  Ser  Thr  Val  Lys  Glu
545                           550                      555
```

( 2 ) INFORMATION FOR SEQ ID NO:13:

( i ) SEQUENCE CHARACTERISTICS:
        ( A ) LENGTH: 2315 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR79 (XR79.SEQ)

( i x ) FEATURE:
        ( A ) NAME/KEY: CDS
        ( B ) LOCATION: 204..2009

( x i ) SEQUENCE DESCRIPTION: SEQ ID NO:13:

```
GCGTTAGAAA  AGGTTCAAAA  TAGGCACAAA  GTCGTGAAAA  TATCGTAACT  GACCGGAAGT      60

AACATAACTT  TAACCAAGTG  CCTCGAAAAA  TAGATGTTTT  TAAAAGCTCA  AGAATGGTGA     120

TAACAGACGT  CCAATAAGAA  TTTTCAAAGA  GCCAATTATT  TATACAGCCG  ACGACTATTT     180

TTTAGCCGCC  TGCTGTGGCG  ACA ATG GAC GGC GTT AAG GTT GAG ACG TTC            230
                            Met Asp Gly Val Lys Val Glu Thr Phe
                             1               5

ATC AAA AGC GAA GAA AAC CGA GCG ATG CCC TTG ATC GGA GGA GGC AGT            278
Ile Lys Ser Glu Glu Asn Arg Ala Met Pro Leu Ile Gly Gly Gly Ser
 10              15                  20                  25

GCC TCA GGC GGC ACT CCT CTG CCA GGA GGC GTG GGA ATG GGA GCC                326
Ala Ser Gly Gly Thr Pro Leu Pro Gly Gly Val Gly Met Gly Ala
         30                  35                  40

GGA GCA TCC GCA ACG TTG AGC GTG GAG CTG TGT TTG GTG TGC GGG GAC            374
Gly Ala Ser Ala Thr Leu Ser Val Glu Leu Cys Leu Val Cys Gly Asp
             45                  50                  55

CGC GCC TCC GGG CGG CAC TAC GGA GCC ATA AGC TGC GAA GGC TGC AAG            422
Arg Ala Ser Gly Arg His Tyr Gly Ala Ile Ser Cys Glu Gly Cys Lys
         60                  65                  70

GGA TTC TTC AAG CGC TCG ATC CGG AAG CAG CTG GGC TAC CAG TGT CGC            470
Gly Phe Phe Lys Arg Ser Ile Arg Lys Gln Leu Gly Tyr Gln Cys Arg
     75                  80                  85

GGG GCT ATG AAC TGC GAG GTC ACC AAG CAC CAC AGG AAT CGG TGC CAG            518
Gly Ala Met Asn Cys Glu Val Thr Lys His His Arg Asn Arg Cys Gln
 90                  95                 100                 105

TTC TGT CGA CTA CAG AAG TGC CTG GCC AGC GGC ATG CGA AGT GAT TCT            566
Phe Cys Arg Leu Gln Lys Cys Leu Ala Ser Gly Met Arg Ser Asp Ser
                110                 115                 120

GTG CAG CAC GAG AGG AAA CCG ATT GTG GAC AGG AAG GAG GGG ATC ATC            614
Val Gln His Glu Arg Lys Pro Ile Val Asp Arg Lys Glu Gly Ile Ile
            125                 130                 135

GCT GCT GCC GGT AGC TCA TCC ACT TCT GGC GGC GGT AAT GGC TCG TCC            662
Ala Ala Ala Gly Ser Ser Ser Thr Ser Gly Gly Gly Asn Gly Ser Ser
        140                 145                 150

ACC TAC CTA TCC GGC AAG TCC GGC TAT CAG CAG GGG CGT GGC AAG GGG            710
Thr Tyr Leu Ser Gly Lys Ser Gly Tyr Gln Gln Gly Arg Gly Lys Gly
    155                 160                 165
```

```
CAC AGT GTA AAG GCC GAA TCC GCG CCA CGC CTC CAG TGC ACA GCG CGC       758
His Ser Val Lys Ala Glu Ser Ala Pro Arg Leu Gln Cys Thr Ala Arg
170             175             180             185

CAG CAA CGG GCC TTC AAT TTG AAT GCA GAA TAT ATT CCG ATG GGT TTG       806
Gln Gln Arg Ala Phe Asn Leu Asn Ala Glu Tyr Ile Pro Met Gly Leu
            190             195             200

AAT TTC GCA GAA CTA ACG CAG ACA TTG ATG TTC GCT ACC CAA CAG CAG       854
Asn Phe Ala Glu Leu Thr Gln Thr Leu Met Phe Ala Thr Gln Gln Gln
            205             210             215

CAG CAA CAA CAG CAA CAG CAT CAA CAG AGT GGT AGC TAT TCG CCA GAT       902
Gln Gln Gln Gln Gln Gln His Gln Gln Ser Gly Ser Tyr Ser Pro Asp
            220             225             230

ATT CCG AAG GCA GAT CCC GAG GAT GAC GAG GAC GAC TCA ATG GAC AAC       950
Ile Pro Lys Ala Asp Pro Glu Asp Asp Glu Asp Asp Ser Met Asp Asn
235             240             245

AGC AGC ACG CTG TGC TTG CAG TTG CTC GCC AAC AGC GCC AGC AAC AAC       998
Ser Ser Thr Leu Cys Leu Gln Leu Leu Ala Asn Ser Ala Ser Asn Asn
250             255             260             265

AAC TCG CAG CAC CTG AAC TTT AAT GCT GGG GAA GTA CCC ACC GCT CTG      1046
Asn Ser Gln His Leu Asn Phe Asn Ala Gly Glu Val Pro Thr Ala Leu
            270             275             280

CCT ACC ACC TCG ACA ATG GGG CTT ATT CAG AGT TCG CTG GAC ATG CGG      1094
Pro Thr Thr Ser Thr Met Gly Leu Ile Gln Ser Ser Leu Asp Met Arg
            285             290             295

GTC ATC CAC AAG GGA CTG CAG ATC CTG CAG CCC ATC CAA AAC CAA CTG      1142
Val Ile His Lys Gly Leu Gln Ile Leu Gln Pro Ile Gln Asn Gln Leu
            300             305             310

GAG CGA AAT GGT AAT CTG AGT GTG AAG CCC GAG TGC GAT TCA GAG GCG      1190
Glu Arg Asn Gly Asn Leu Ser Val Lys Pro Glu Cys Asp Ser Glu Ala
315             320             325

GAG GAC AGT GGC ACC GAG GAT GCC GTA GAC GCG GAG CTG GAG CAC ATG      1238
Glu Asp Ser Gly Thr Glu Asp Ala Val Asp Ala Glu Leu Glu His Met
330             335             340             345

GAA CTA GAC TTT GAG TGC GGT GGG AAC CGA AGC GGT GGA AGC GAT TTT      1286
Glu Leu Asp Phe Glu Cys Gly Gly Asn Arg Ser Gly Gly Ser Asp Phe
            350             355             360

GCT ATC AAT GAG GCG GTC TTT GAA CAG GAT CTT CTC ACC GAT GTG CAG      1334
Ala Ile Asn Glu Ala Val Phe Glu Gln Asp Leu Leu Thr Asp Val Gln
            365             370             375

TGT GCC TTT CAT GTG CAA CCG CCG ACT TTG GTC CAC TCG TAT TTA AAT      1382
Cys Ala Phe His Val Gln Pro Pro Thr Leu Val His Ser Tyr Leu Asn
            380             385             390

ATT CAT TAT GTG TGT GAG ACG GGC TCG CGA ATC ATT TTT CTC ACC ATC      1430
Ile His Tyr Val Cys Glu Thr Gly Ser Arg Ile Ile Phe Leu Thr Ile
395             400             405

CAT ACC CTT CGA AAG GTT CCA GTT TTC GAA CAA TTG GAA GCC CAT ACA      1478
His Thr Leu Arg Lys Val Pro Val Phe Glu Gln Leu Glu Ala His Thr
410             415             420             425

CAG GTG AAA CTC CTG AGA GGA GTG TGG CCA GCA TTA ATG GCT ATA GCT      1526
Gln Val Lys Leu Leu Arg Gly Val Trp Pro Ala Leu Met Ala Ile Ala
            430             435             440

TTG GCG CAG TGT CAG GGT CAG CTT TCG GTG CCC ACC ATT ATC GGG CAG      1574
Leu Ala Gln Cys Gln Gly Gln Leu Ser Val Pro Thr Ile Ile Gly Gln
            445             450             455

TTT ATT CAA AGC ACT CGC CAG CTA GCG GAT ATC GAT AAG ATC GAA CCG      1622
Phe Ile Gln Ser Thr Arg Gln Leu Ala Asp Ile Asp Lys Ile Glu Pro
            460             465             470

TTG AAG ATC TCG AAG ATG GCA AAT CTC ACC AGG ACC CTG CAC GAC TTT      1670
Leu Lys Ile Ser Lys Met Ala Asn Leu Thr Arg Thr Leu His Asp Phe
475             480             485
```

-continued

| | | | | | | | | | | | | | | | | |
|--|--|--|--|--|--|--|--|--|--|--|--|--|--|--|--|--|
| GTC | CAG | GAG | CTC | CAG | TCA | CTG | GAT | GTT | ACT | GAT | ATG | GAG | TTT | GGC | TTG | 1718 |
| Val | Gln | Glu | Leu | Gln | Ser | Leu | Asp | Val | Thr | Asp | Met | Glu | Phe | Gly | Leu | |
| 490 | | | | 495 | | | | | 500 | | | | | 505 | | |
| CTG | CGT | CTG | ATC | TTG | CTC | TTC | AAT | CCA | ACG | CTC | TTC | CAG | CAT | CGC | AAG | 1766 |
| Leu | Arg | Leu | Ile | Leu | Leu | Phe | Asn | Pro | Thr | Leu | Phe | Gln | His | Arg | Lys | |
| | | | | 510 | | | | | 515 | | | | | 520 | | |
| GAG | CGG | TCG | TTG | CGA | GGC | TAC | GTC | CGC | AGA | GTC | CAA | CTC | TAC | GCT | CTG | 1814 |
| Glu | Arg | Ser | Leu | Arg | Gly | Tyr | Val | Arg | Arg | Val | Gln | Leu | Tyr | Ala | Leu | |
| | | | | 525 | | | | | 530 | | | | | 535 | | |
| TCA | AGT | TTG | AGA | AGG | CAG | GGT | GGC | ATC | GGC | GGC | GGC | GAG | GAG | CGC | TTT | 1862 |
| Ser | Ser | Leu | Arg | Arg | Gln | Gly | Gly | Ile | Gly | Gly | Gly | Glu | Glu | Arg | Phe | |
| | | | 540 | | | | | 545 | | | | | 550 | | | |
| AAT | GTT | CTG | GTG | GCT | CGC | CTT | CTT | CCG | CTC | AGC | AGC | CTG | GAC | GCA | GAG | 1910 |
| Asn | Val | Leu | Val | Ala | Arg | Leu | Leu | Pro | Leu | Ser | Ser | Leu | Asp | Ala | Glu | |
| | 555 | | | | | 560 | | | | | 565 | | | | | |
| GCC | ATG | GAG | GAG | CTG | TTC | TTC | GCC | AAC | TTG | GTG | GGG | CAG | ATG | CAG | ATG | 1958 |
| Ala | Met | Glu | Glu | Leu | Phe | Phe | Ala | Asn | Leu | Val | Gly | Gln | Met | Gln | Met | |
| 570 | | | | | 575 | | | | | 580 | | | | | 585 | |
| GAT | GCT | CTT | ATT | CCG | TTC | ATA | CTG | ATG | ACC | AGC | AAC | ACC | AGT | GGA | CTG | 2006 |
| Asp | Ala | Leu | Ile | Pro | Phe | Ile | Leu | Met | Thr | Ser | Asn | Thr | Ser | Gly | Leu | |
| | | | | 590 | | | | | 595 | | | | | 600 | | |

| | | |
|--|--|--|
| TAGGCGGAAT TGAGAAGAAC AGGGCGCAAG CAGATTCGCT AGACTGCCCA AAAGCAAGAC | 2066 |
| TGAAGATGGA CCAAGTGCGG GCAATACATG TAGCAACTAG GCAAATCCCA TTAATTATAT | 2126 |
| ATTAATATA TACAATATAT AGTTTAGGAT ACAATATTCT AACATAAAAC CATGAGTTTA | 2186 |
| TTGTTGTTCA CAGATAAAAT GGAATCGATT TCCCAATAAA AGCGAATATG TTTTAAACA | 2246 |
| GAATGTTTGC ATCAGAACTT TGAGATGTAT ACATTAGATT ATTACAACAC AAAAAAAAA | 2306 |
| AAAAAAAA | 2315 |

( 2 ) INFORMATION FOR SEQ ID NO:14:

( i ) SEQUENCE CHARACTERISTICS:
        ( A ) LENGTH: 601 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|--|--|--|--|--|--|--|--|--|--|--|--|--|--|--|
| Met | Asp | Gly | Val | Lys | Val | Glu | Thr | Phe | Ile | Lys | Ser | Glu | Glu | Asn | Arg |
| 1 | | | | 5 | | | | | 10 | | | | | 15 | |
| Ala | Met | Pro | Leu | Ile | Gly | Gly | Gly | Ser | Ala | Ser | Gly | Gly | Thr | Pro | Leu |
| | | | 20 | | | | | 25 | | | | | 30 | | |
| Pro | Gly | Gly | Gly | Val | Gly | Met | Gly | Ala | Gly | Ala | Ser | Ala | Thr | Leu | Ser |
| | | | 35 | | | | | 40 | | | | | 45 | | |
| Val | Glu | Leu | Cys | Leu | Val | Cys | Gly | Asp | Arg | Ala | Ser | Gly | Arg | His | Tyr |
| | 50 | | | | | 55 | | | | | 60 | | | | |
| Gly | Ala | Ile | Ser | Cys | Glu | Gly | Cys | Lys | Gly | Phe | Phe | Lys | Arg | Ser | Ile |
| 65 | | | | | 70 | | | | | 75 | | | | | 80 |
| Arg | Lys | Gln | Leu | Gly | Tyr | Gln | Cys | Arg | Gly | Ala | Met | Asn | Cys | Glu | Val |
| | | | | 85 | | | | | 90 | | | | | 95 | |
| Thr | Lys | His | His | Arg | Asn | Arg | Cys | Gln | Phe | Cys | Arg | Leu | Gln | Lys | Cys |
| | | | 100 | | | | | 105 | | | | | 110 | | |
| Leu | Ala | Ser | Gly | Met | Arg | Ser | Asp | Ser | Val | Gln | His | Glu | Arg | Lys | Pro |
| | | 115 | | | | | 120 | | | | | 125 | | | |
| Ile | Val | Asp | Arg | Lys | Glu | Gly | Ile | Ile | Ala | Ala | Gly | Ser | Ser | Ser |
| | 130 | | | | | 135 | | | | | 140 | | | | |

```
Thr  Ser  Gly  Gly  Gly  Asn  Gly  Ser  Ser  Thr  Tyr  Leu  Ser  Gly  Lys  Ser
145                 150                      155                      160

Gly  Tyr  Gln  Gln  Gly  Arg  Gly  Lys  Gly  His  Ser  Val  Lys  Ala  Glu  Ser
                    165                      170                      175

Ala  Pro  Arg  Leu  Gln  Cys  Thr  Ala  Arg  Gln  Gln  Arg  Ala  Phe  Asn  Leu
               180                      185                      190

Asn  Ala  Glu  Tyr  Ile  Pro  Met  Gly  Leu  Asn  Phe  Ala  Glu  Leu  Thr  Gln
          195                      200                      205

Thr  Leu  Met  Phe  Ala  Thr  Gln  Gln  Gln  Gln  Gln  Gln  Gln  Gln  Gln  His
     210                      215                      220

Gln  Gln  Ser  Gly  Ser  Tyr  Ser  Pro  Asp  Ile  Pro  Lys  Ala  Asp  Pro  Glu
225                 230                      235                      240

Asp  Asp  Glu  Asp  Asp  Ser  Met  Asp  Asn  Ser  Ser  Thr  Leu  Cys  Leu  Gln
               245                      250                      255

Leu  Leu  Ala  Asn  Ser  Ala  Ser  Asn  Asn  Asn  Ser  Gln  His  Leu  Asn  Phe
          260                      265                      270

Asn  Ala  Gly  Glu  Val  Pro  Thr  Ala  Leu  Pro  Thr  Thr  Ser  Thr  Met  Gly
          275                      280                      285

Leu  Ile  Gln  Ser  Ser  Leu  Asp  Met  Arg  Val  Ile  His  Lys  Gly  Leu  Gln
     290                      295                      300

Ile  Leu  Gln  Pro  Ile  Gln  Asn  Gln  Leu  Glu  Arg  Asn  Gly  Asn  Leu  Ser
305                 310                      315                      320

Val  Lys  Pro  Glu  Cys  Asp  Ser  Glu  Ala  Glu  Asp  Ser  Gly  Thr  Glu  Asp
               325                      330                      335

Ala  Val  Asp  Ala  Glu  Leu  Glu  His  Met  Glu  Leu  Asp  Phe  Glu  Cys  Gly
               340                      345                      350

Gly  Asn  Arg  Ser  Gly  Gly  Ser  Asp  Phe  Ala  Ile  Asn  Glu  Ala  Val  Phe
          355                      360                      365

Glu  Gln  Asp  Leu  Leu  Thr  Asp  Val  Gln  Cys  Ala  Phe  His  Val  Gln  Pro
     370                      375                      380

Pro  Thr  Leu  Val  His  Ser  Tyr  Leu  Asn  Ile  His  Tyr  Val  Cys  Glu  Thr
385                 390                      395                      400

Gly  Ser  Arg  Ile  Ile  Phe  Leu  Thr  Ile  His  Thr  Leu  Arg  Lys  Val  Pro
                    405                      410                      415

Val  Phe  Glu  Gln  Leu  Glu  Ala  His  Thr  Gln  Val  Lys  Leu  Leu  Arg  Gly
               420                      425                      430

Val  Trp  Pro  Ala  Leu  Met  Ala  Ile  Ala  Leu  Ala  Gln  Cys  Gln  Gly  Gln
          435                      440                      445

Leu  Ser  Val  Pro  Thr  Ile  Ile  Gly  Gln  Phe  Ile  Gln  Ser  Thr  Arg  Gln
     450                      455                      460

Leu  Ala  Asp  Ile  Asp  Lys  Ile  Glu  Pro  Leu  Lys  Ile  Ser  Lys  Met  Ala
465                 470                      475                      480

Asn  Leu  Thr  Arg  Thr  Leu  His  Asp  Phe  Val  Gln  Glu  Leu  Gln  Ser  Leu
               485                      490                      495

Asp  Val  Thr  Asp  Met  Glu  Phe  Gly  Leu  Leu  Arg  Leu  Ile  Leu  Leu  Phe
               500                      505                      510

Asn  Pro  Thr  Leu  Phe  Gln  His  Arg  Lys  Glu  Arg  Ser  Leu  Arg  Gly  Tyr
          515                      520                      525

Val  Arg  Arg  Val  Gln  Leu  Tyr  Ala  Leu  Ser  Ser  Leu  Arg  Arg  Gln  Gly
     530                      535                      540

Gly  Ile  Gly  Gly  Gly  Glu  Glu  Arg  Phe  Asn  Val  Leu  Val  Ala  Arg  Leu
545                 550                      555                      560

Leu  Pro  Leu  Ser  Ser  Leu  Asp  Ala  Glu  Ala  Met  Glu  Glu  Leu  Phe  Phe
               565                      570                      575
```

```
Ala  Asn  Leu  Val  Gly  Gln  Met  Gln  Met  Asp  Ala  Leu  Ile  Pro  Phe  Ile
               580                 585                     590
Leu  Met  Thr  Ser  Asn  Thr  Ser  Gly  Leu
               595                 600
```

ORPHAN STEROID HORMONE RECEPTORS

This application is a divisional of application Ser. No. 08/333,358, filed Nov. 2, 1994, now U.S. Pat. No. 5,571,696, which is continuation of application Ser. No. 07/761,068, now abandoned.

FIELD OF THE INVENTION

The present invention relates to novel steroid-hormone or steroid-hormone like receptor proteins, genes encoding such proteins, and methods of making and using such proteins. In a particular aspect, the present invention relates to bioassay systems for determining the selectivity of interaction between ligands and steroid-hormone or steroid-hormone like receptor proteins.

BACKGROUND OF THE INVENTION

Transcriptional regulation of development and homeostasis in complex eukaryotes, including humans and other mammals, birds, fish, insects, and the like, is controlled by a wide variety of regulatory substances, including steroid and thyroid hormones. These hormones exert potent effects on development and differentiation of phylogenetically diverse organisms. The effects of hormones are mediated by interaction with specific, high affinity binding proteins referred to as receptors.

The ability to identify additional compounds which are able to affect transcription of genes which are responsive to steroid hormones or metabolites thereof, would be of significant value in identifying compounds of potential therapeutic use. Further, systems useful for monitoring solutions, body fluids, and the like, for the presence of steroid hormones or metabolites thereof, would be of value in medical diagnosis, as well as for various biochemical applications.

A number of receptor proteins, each specific for one of several classes of cognate steroid hormones [e.g., estrogens (estrogen receptor), progesterones (progesterone receptor), glucocorticoid (glucocorticoid receptor), androgens (androgen receptor), aldosterones (mineralocorticoid receptor), vitamin D (vitamin D receptor)], retinoids (e.g., retinoic acid receptor) or for cognate thyroid hormones (e.g., thyroid hormone receptor), are known. Receptor proteins have been found to be distributed throughout the cell population of complex eukaryotes in a tissue specific fashion.

Molecular cloning studies have made it possible to demonstrate that receptors for steroid, retinoid and thyroid hormones are all structurally related and comprise a superfamily of regulatory proteins. These regulatory proteins are capable of modulating specific gene expression in response to hormone stimulation by binding directly to cis-acting elements. Structural comparisons and functional studies with mutant receptors have revealed that these molecules are composed of a series of discrete functional domains, most notably, a DNA-binding domain that is composed typically of 66–68 amino acids, including two zinc fingers and an associated carboxy terminal stretch of approximately 250 amino acids, which latter region comprises the ligand-binding domain.

An important advance in the characterization of this superfamily of regulatory proteins has been the delineation of a growing list of gene products which possess the structural features of hormone receptors. This growing list of gene products has been isolated by low-stringency hybridization techniques employing DNA sequences encoding previously identified hormone receptor proteins.

It is known that steroid or thyroid hormones, protected forms thereof, or metabolites thereof, enter cells and bind to the corresponding specific receptor protein, initiating an allosteric alteration of the protein. As a result of this alteration, the complex of receptor and hormone (or metabolite thereof) is capable of binding to certain specific sites on chromatin with high affinity.

It is also known that many of the primary effects of steroid and thyroid hormones involve increased transcription of a subset of genes in specific cell types.

A number of steroid hormone- and thyroid hormone-responsive transcriptional control units have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic $\alpha_{2u}$-globulin gene transcriptional control units, responsive to androgens, estrogens, thyroid hormones, and glucocorticoids.

A major obstacle to further understanding and more widespread use of the various members of the steroid/thyroid superfamily of hormone receptors has been a lack of availability of the receptor proteins, in sufficient quantity and sufficiently pure form, to allow them to be adequately characterized. The same is true for the DNA gene segments which encode them. Lack of availability of these DNA segments has prevented in vitro manipulation and in vivo expression of the receptor-encoding genes, and consequently the knowledge such manipulation and expression would yield.

In addition, a further obstacle to a more complete understanding and more widespread use of members of the steroid/thyroid receptor superfamily is the fact that additional members of this superfamily remain to be discovered, isolated and characterized.

The present invention is directed to overcoming these problems of short supply of adequately purified receptor material, lack of DNA segments which encode such receptors and increasing the number of identified and characterized hormone receptors which are available for use.

BRIEF DESCRIPTION OF THE INVENTION

In accordance with the present invention, we have discovered novel members of the steroid/thyroid superfamily of receptors. The novel receptors of the present invention are soluble, intracellular, nuclear (as opposed to cell surface) receptors, which are activated to modulate transcription of certain genes in animal cells when the cells are exposed to ligands therefor. The nuclear receptors of the present invention differ significantly from known steroid receptors, both in primary sequence and in responsiveness to exposure of cells to various ligands, e.g., steroids or steroid-like compounds.

Also provided in accordance with the present invention are DNAs encoding the receptors of the present invention, including expression vectors for expression thereof in animal cells, cells transformed with such expression vectors, cells co-transformed with such expression vectors and reporter vectors (to monitor the ability of the receptors to modulate transcription when the cells are exposed to a compound which interacts with the receptor); and methods of using such co-transformed cells in screening for compounds which are capable of leading to modulation of receptor activity.

Further provided in accordance with the present invention are DNA and RNA probes for identifying DNAs encoding additional steroid receptors.

In accordance with yet another embodiment of the invention, there is provided a method for making the receptors of the invention by expressing DNAs which encode the receptors in suitable host organisms.

The novel receptors and DNAs encoding same can be employed for a variety of purposes. For example, novel receptors of the present invention can be included as part of a panel of receptors which are screened to determine the selectivity of interaction of proposed agonists or antagonists and other receptors. Thus, a compound which is believed to interact selectively, for example, with the glucocorticoid receptor, should not have any substantial effect on any other receptors, including those of the present invention. Conversely, if such a proposed compound does interact with one or more of the invention receptors, then the possibility of side reactions caused by such compound is clearly indicated.

DETAILED DESCRIPTION OF THE INVENTION

Figure 1:
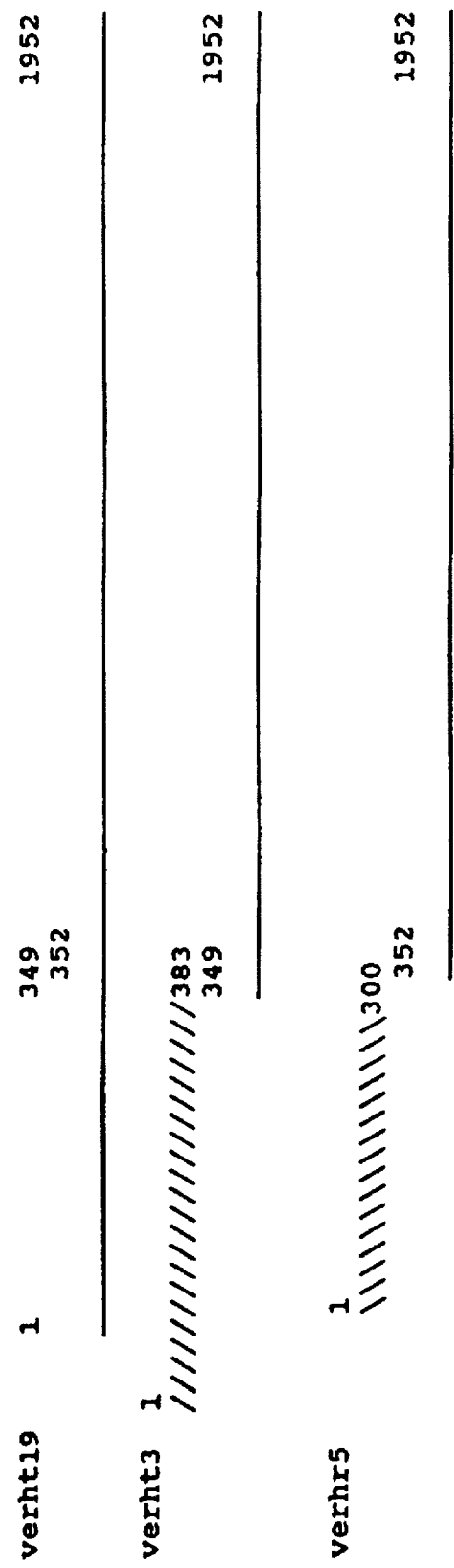
FIG. 1 is a schematic diagram correlating the relationship between the alternate spliced variants of invention receptor XR1.

In accordance with the present invention, there are provided DNAs encoding a polypeptide characterized by having a DNA binding domain comprising about 66 amino acids with 9 cysteine (Cys) residues, wherein said DNA binding domain has:

(i) less than about 70% amino acid sequence identity with the DNA binding domain of human retinoic acid receptor-alpha (hRAR-alpha);

(ii) less than about 60% amino acid sequence identity with the DNA binding domain of human thyroid receptor-beta (hTR-beta);

(iii) less than about 50% amino acid sequence identity with the DNA binding domain of human glucocorticoid receptor (hGR); and (iv) less than about 65% amino acid sequence identity in with the DNA binding domain of human retinoid X receptor-alpha (hRXR-alpha).

Alternatively, DNAs of the invention can be characterized with respect to percent amino acid sequence identity of the ligand binding domain of polypeptides encoded thereby, relative to amino acid sequences of previously characterized receptors. As yet another alternative, DNAs of the invention can be characterized by the percent overall amino acid sequence identity of polypeptides encoded thereby, relative to amino acid sequences of previously characterized receptors.

Thus, DNAs of the invention can be characterized as encoding polypeptides having, in the ligand binding domain:

(i) less than about 35% amino acid sequence identity with the ligand binding domain of hRAR-alpha;

(ii) less than about 30% amino acid sequence identity with the ligand binding domain of hTR-beta;

(iii) less than about 25% amino acid sequence identity with the ligand binding domain of hGR; and (iv) less than about 30% amino acid sequence identity with the ligand binding domain of hRXR-alpha.

DNAs of the invention can be further characterized as encoding polypeptides having an overall amino acid sequence identity of:

(i) less than about 35% relative to hRAR-alpha;
(ii) less than about 35% relative to hTR-beta;
(iii) less than about 25% relative to hGR; and
(iv) less than about 35% relative to hRXR-alpha.

Specific receptors contemplated for use in the practice of the present invention include:

"XR1" (variously referred to herein as receptor "XR1", "hXR1", "hXR1.pep" or "verHT19.pep";
wherein the prefix "h" indicates the clone is of human origin), a polypeptide characterized as
having a DNA binding domain comprising:
(i) about 68% amino acid sequence identity with the DNA binding domain of hRAR-alpha;
(ii) about 59% amino acid sequence identity with the DNA binding domain of hTR-beta;
(iii) about 45% amino acid sequence identity with the DNA binding domain of hGR; and
(iv) about 65% amino acid sequence identity with the DNA binding domain of hRXR-alpha;

see also Sequence ID No. 2 for a specific amino acid sequence representative of XR1, as well as Sequence ID No. 1 which is an exemplary nucleotide sequence encoding XR1. In addition, Sequence ID Nos. 4 and 6 present alternate amino terminal sequences for the clone referred to as XR1 (the variant referred to as verht3 is presented in Sequence ID No. 4 (an exemplary nucleotide sequence encoding such variant presented in Sequence ID No. 3), and the variant referred to as verhr5 is presented in Sequence ID No. 6 (an exemplary nucleotide sequence encoding such variant presented in Sequence ID No. 5);

"XR2" (variously referred to herein as receptor "XR2", "hXR2" or "hXR2.pep"), a polypeptide characterized as having a DNA binding domain comprising:
(i) about 55% amino acid sequence identity with the DNA binding domain of hRAR-alpha;
(ii) about 56% amino acid sequence identity with the DNA binding domain of hTR-beta;
(iii) about 50% amino acid sequence identity with the DNA binding domain of hGR; and
(iv) about 52% amino acid sequence identity with the DNA binding domain of hRXR-alpha;

see also Sequence ID No. 8 for a specific amino acid sequence representative of XR2, as well as Sequence ID No. 7 which is an exemplary nucleotide sequence encoding XR2;

"XR4" (variously referred to herein as receptor "XR4", "mXR4" or "mXR4.pep"; wherein the prefix "m" indicates the clone is of mouse origin), a polypeptide characterized as having a DNA binding domain comprising:
(i) about 62% amino acid sequence identity with the DNA binding domain of hRAR-alpha;
(ii) about 58% amino acid sequence identity with the DNA binding domain of hTR-beta;
(iii) about 48% amino acid sequence identity with the DNA binding domain of hGR; and
(iv) about 62% amino acid sequence identity with the DNA binding domain of hRXR-alpha;

see also Sequence ID No. 10 for a specific amino acid sequence representative of XR4, as well as Sequence ID No. 9 which is an exemplary nucleotide sequence encoding XR4;

"XR5" (variously referred to herein as receptor "XR5", "mXR5" or "mXR5.pep"), a polypeptide characterized as having a DNA binding domain comprising:
(i) about 59% amino acid sequence identity with the DNA binding domain of hRAR-alpha;
(ii) about 52% amino acid sequence identity with the DNA binding domain of hTR-beta;
(iii) about 44% amino acid sequence identity with the DNA binding domain of hGR; and
(iv) about 61% amino acid sequence identity with the DNA binding domain of hRXR-alpha;
see also Sequence ID No. 12 for a specific amino acid sequence representative of XR5, as well as Sequence ID No. 11 which is an exemplary nucleotide sequence encoding XR5; and "XR79" (variously referred to herein as "XR79", "dXR79" or "dXR79.pep"; wherein the prefix "d" indicates the clone is of Drosophila origin), a polypeptide characterized as having a DNA binding domain comprising:
(i) about 59% amino acid sequence identity with the DNA binding domain of hRAR-alpha;
(ii) about 55% amino acid sequence identity with the DNA binding domain of hTR-beta;
(iii) about 50% amino acid sequence identity with the DNA binding domain of hGR; and
(iv) about 65% amino acid sequence identity with the DNA binding domain of hRXR-alpha;
see also Sequence ID No. 14 for a specific amino acid sequence representative of XR79, as well as Sequence ID No. 13 which is an exemplary nucleotide sequence encoding XR79.

The receptor referred to herein as "XR1" is observed as three closely related proteins, presumably produced by alternate splicing from a single gene. The first of these proteins to be characterized (referred to as "verht19") comprises about 548 amino acids, and has a $M_r$ of about 63 kilodalton. Northern analysis indicates that a single mRNA species corresponding to XR1 is highly expressed in the brain. A variant of verht19 (alternatively referred to as "verht3", XR1' or XR1prime) is further characterized as comprising about 556 amino acids, and having a $M_r$ of about 64 kilodalton. Yet another variant of verht19 (alternatively referred to as "verhr5", XR1" or XR1prim2) is further characterized as comprising about 523 amino acids, and having a $M_r$ of about 60 kilodalton. The interrelationship between these three variants of XR1 is illustrated schematically in FIG. 1.

The receptor referred to herein as "XR2" is further characterized as a protein comprising about 440 amino acids, and having a $M_r$ of about 50 kilodalton. Northern analysis indicates that a single mRNA species (~1.7 kb) corresponding to XR2 is expressed most highly in liver, kidney, lung, intestine and adrenals of adult male rats. Transactivation studies (employing chimeric receptors containing the XR2 DNA binding domain and the ligand binding domain of a prior art receptor) indicate that XR2 is capable of binding to TREt. In terms of amino acid sequence identity with prior art receptors, XR2 is most closely related to the vitamin D receptor (39% overall amino acid sequence identity, 17% amino acid identity in the amino terminal domain of the receptor, 53% amino acid identity in the DNA binding domain of the receptor and 37% amino acid identity in the ligand binding domain of the receptor).

The receptor referred to herein as "XR4" is further characterized as a protein comprising about 439 amino acids, and having a $M_r$ of about 50 kilodalton. In terms of amino acid sequence identity with prior art receptors, XR4 is most closely related to the peroxisome proliferator-activated receptor (62% overall amino acid sequence identity, 30% amino acid identity in the amino terminal domain of the receptor, 86% amino acid identity in the DNA binding domain of the receptor and 64% amino acid identity in the ligand binding domain of the receptor). XR4 is expressed ubiquitously and throughout development (as determined by in situ hybridization).

The receptor referred to herein as "XR5" is further characterized as a protein comprising about 556 amino acids, and having a $M_r$ of about 64 kilodalton. In situ hybridization reveals widespread expression throughout development. High levels of expression are observed in the embryonic liver around day 12, indicating a potential role in haematopoiesis. High levels are also found in maturing dorsal root ganglia and in the skin. In terms of amino acid sequence identity with prior art receptors, XR5 is most closely related to the rat nerve growth factor induced protein-B (NGFI-B) receptor. With respect to NGFI-B, XR5 has 29% overall amino acid sequence identity, 15% amino acid identity in the amino terminal domain of the receptor, 52% amino acid identity in the DNA binding domain of the receptor and 29% amino acid identity in the ligand binding domain of the receptor.

The receptor referred to herein as "XR79" is further characterized as a protein comprising about 601 amino acids, and having a $M_r$ of about 66 kilodalton. Whole mount in situ hybridization reveals a fairly uniform pattern of RNA expression during embryogenesis. Northern blot analysis indicates that a 2.5 kb transcript corresponding to XR79 is present in RNA throughout development. The levels of XR79 mRNA are highest in RNA from 0–3 hour old embryos, i.e., maternal product, and lowest in RNA from the second instar larvae (L2 stage). In situ hybridization reveals that XR79 is distributed relatively uniformly at different stages of embryogenesis. In terms of amino acid sequence identity with prior art receptors, XR79 is most closely related to the mammalian receptor TR2 (see Chang and Kokontis in Biochemical and Biophysical Research Communications 155: 971–977 (1988)), as well as members of the coup family, i.e., ear2, coup(ear3), harp-1. With respect to TR2, XR79 has 33% overall amino acid sequence identity, 16% amino acid identity in the amino terminal domain of the receptor, 74% amino acid identity in the DNA binding domain of the receptor and 28% amino acid identity in the ligand binding domain of the receptor. With respect to coup (ear3) (see Miyajima et al., in Nucl Acids Res 16: 11057–11074 (1988), XR79 has 32% overall amino acid sequence identity, 21% amino acid identity in the amino terminal domain of the receptor, 62% amino acid identity in the DNA binding domain of the receptor and 22% amino acid identity in the ligand binding domain of the receptor.

In accordance with a specific embodiment of the present invention, there is provided an expression vector which comprises DNA as previously described (or functional fragments thereof), and which further comprises:

at the 5'-end of said DNA, a promoter and a nucleotide triplet encoding a translational start codon, and at the 3'-end of said DNA, a nucleotide triplet encoding a translational stop codon;

wherein said expression vector is operative in a cell in culture (e.g., yeast, bacteria, mammalian) to express the protein encoded by said DNA.

As employed herein, reference to "functional fragments" embraces DNA encoding portions of the invention receptors which retain one or more of the functional characteristics of steroid hormone or steroid hormone-like receptors, e.g., DNA binding properties of such receptors, ligand binding properties of such receptors, the ability to heterodimerize, nuclear localization properties of such receptors, phosphorylation properties of such receptors, transactivation domains characteristic of such receptors, and the like.

In accordance with a further embodiment of the present invention, there are provided cells in culture (e.g., yeast, bacteria, mammalian) which are transformed with the above-described expression vector.

In accordance with yet another embodiment of the present invention, there is provided a method of making the above-described novel receptors (or functional fragments thereof) by culturing the above-described cells under conditions suitable for expression of polypeptide product.

In accordance with a further embodiment of the present invention, there are provided novel polypeptide products produced by the above-described method.

In accordance with a still further embodiment of the present invention, there are provided chimeric receptors comprising at least an amino-terminal domain, a DNA-binding domain, and a ligand-binding domain, wherein at least one of the domains thereof is derived from the novel polypeptides of the present invention; and wherein at least one of the domains thereof is derived from at least one previously identified member of the steroid/thyroid superfamily of receptors e.g., glucocorticoid receptor (GR), thyroid receptors (TR), retinoic acid receptors (RAR), mineralocorticoid receptor (MR), estrogen receptor (ER), the estrogen related receptors (e.g., hERR1 or hERR2), retinoid X receptors (e.g., RXRα, RXRβ or RXRδ), vitamin D receptor (VDR), aldosterone receptor (AR), progesterone receptor (PR), the ultraspiracle receptor (USP), nerve growth factor induced protein-B (NGFI-B), the coup family of transcription factors (COUP), peroxisome proliferator-activated receptor (PPAR), mammalian receptor TR2 (TR2), and the like.

In accordance with yet another embodiment of the present invention, there is provided a method of using polypeptides of the invention to screen for response elements and/or ligands for the novel receptors described herein. The method to identify compounds which act as ligands for receptor polypeptides of the invention comprising:

assaying for the presence or absence of reporter protein upon contacting of cells containing a chimeric form of said receptor polypeptide and reporter vector with said compound;

wherein said chimeric form of said receptor polypeptide comprises the ligand binding domain of said receptor polypeptide and the amino-terminal and DNA-binding domains of one or more previously identified members of the steroid/thyroid superfamily of receptors;

wherein said reporter vector comprises:

(a) a promoter that is operable in said cell, (b) a hormone response element which is responsive to the receptor from which the DNA-binding domain of said chimeric form of said receptor polypeptide is derived, and (c) a DNA segment encoding a reporter protein, wherein said reporter protein-encoding DNA segment is operatively linked to said promoter for transcription of said DNA segment, and wherein said hormone response element is operatively linked to said promoter for activation thereof, and thereafter identifying those compounds which induce or block the production of reporter in the presence of said chimeric form of said receptor polypeptide.

The method to identify response elements for receptor polypeptides of the invention comprises:

assaying for the presence or absence of reporter protein upon contacting of cells containing a chimeric form of said receptor polypeptide and reporter vector with a compound which is a known agonist or antagonist for the receptor from which the ligand-binding domain of said chimeric form of said receptor polypeptide is derived;

wherein said chimeric form of said receptor polypeptide comprises the DNA-binding domain of the receptor polypeptide and the amino-terminal and ligand-binding domains of one or more previously identified members of the steroid/thyroid superfamily of receptors;

wherein said reporter vector comprises:

(a) a promoter that is operable in said cell, (b) a putative hormone response element, and (c) a DNA segment encoding a reporter protein, wherein said reporter protein-encoding DNA segment is operatively linked to said promoter for transcription of said DNA segment, and wherein said hormone response element is operatively linked to said promoter for activation thereof; and identifying those response elements for which the production of reporter is induced or blocked in the presence of said chimeric form of said receptor polypeptide.

In accordance with yet another embodiment of the present invention, there is provided a DNA or RNA labeled for detection; wherein said DNA or RNA comprises a nucleic acid segment, preferably of at least 20 bases in length, wherein said segment has substantially the same sequence as a segment of the same length selected from the DNA segment represented by bases 21–1902, inclusive, of Sequence ID No. 1, bases 1–386, inclusive, of Sequence ID No. 3, bases 10–300, inclusive, of Sequence ID No. 5, bases 21–1615, inclusive, of Sequence ID No. 7, bases 21–2000, inclusive, of Sequence ID No. 9, bases 1–2450, inclusive, of Sequence ID No. 11, bases 21–2295, inclusive, of Sequence ID No. 13, or the complement of any of said segments.

In accordance with still another embodiment of the present invention, there are provided methods of testing compound(s) for the ability to regulate transcription-activating effects of a receptor polypeptide, said method comprising assaying for the presence or absence of reporter protein upon contacting of cells containing a receptor polypeptide and reporter vector with said compound;

wherein said receptor polypeptide is characterized by having a DNA binding domain comprising about 66 amino acids with 9 Cys residues, wherein said DNA binding domain has:

(i) less than about 70% amino acid sequence identity with the DNA binding domain of hRAR-alpha;

(ii) less than about 60% amino acid sequence identity with the DNA binding domain of hTR-beta;

(iii) less than about 50% amino acid sequence identity with the DNA binding domain of hGR; and (iv) less than about 65% amino acid sequence identity with the DNA binding domain of hRXR-alpha; and wherein said reporter vector comprises:

(a) a promoter that is operable in said cell, (b) a hormone response element, and (c) a DNA segment encoding a reporter protein, wherein said reporter protein-encoding DNA segment is operatively linked to said promoter for transcription of said DNA segment, and wherein said hormone response element is operatively linked to said promoter for activation thereof.

In accordance with a still further embodiment of the present invention, there is provided a method of testing a compound for its ability to selectively regulate the transcription-activating effects of a specific receptor polypeptide, said method comprising:

assaying for the presence or absence of reporter protein upon contacting of cells containing said receptor polypeptide and reporter vector with said compound;

wherein said receptor polypeptide is characterized by being responsive to the presence of a known ligand for said receptor to regulate the transcription of associated gene(s);

wherein said reporter vector comprises:
 (a) a promoter that is operable in said cell,
 (b) a hormone response element, and
 (c) a DNA segment encoding a reporter protein,
  wherein said reporter protein-encoding DNA segment is operatively linked to said promoter for transcription of said DNA segment, and
  wherein said hormone response element is operatively linked to said promoter for activation thereof; and assaying for the presence or absence of reporter protein upon contacting of cells containing chimeric receptor polypeptide and reporter vector with said compound;

wherein said chimeric receptor polypeptide comprises the ligand binding domain of a novel receptor of the present invention, and the DNA binding domain of said specific receptor; and thereafter selecting those compounds which induce or block the production of reporter in the presence of said specific receptor, but are substantially unable to induce or block the production of reporter in the presence of said chimeric receptor.

The above-described methods of testing compounds for the ability to regulate transcription-activating effects of invention receptor polypeptides can be carried out employing methods described in U.S. Ser. No. 108,471; now U.S. Pat. No. 5,071,773; filed Oct. 20, 1987, the entire contents of which are hereby incorporated by reference herein.

As employed herein, the term "expression vector" refers to constructs containing DNA of the invention (or functional fragments thereof), plus all sequences necessary for manipulation and expression of such DNA. Such an expression vector will contain both a "translational start site" and a "translational stop site". Those of skill in the art can readily identify sequences which act as either translational start sites or translational stop sites.

Suitable host cells for use in the practice of the present invention include prokaroytic and eukaryote cells, e.g., bacteria, yeast, mammalian cells and the like.

Labeled DNA or RNA contemplated for use in the practice of the present invention comprises nucleic acid sequences covalently attached to readily analyzable species such as, for example, radiolabel (e.g., $^{32}P$, $^{3}H$, $^{35}S$, and the like), enzymatically active label, and the like.

The invention will now be described in greater detail by reference to the following non-limiting examples.

EXAMPLES

Example I

ISOLATION AND CHARACTERIZATION OF XR1

The KpnI/SacI restriction fragment (503bp) including the DNA-binding domain of hRAR-alpha-encoding DNA (See Giguere et al., Nature 330: 624–629 (1987); and commonly assigned U.S. patent application Ser. No. 276,536; now U.S. Pat. No. 4,981,784; filed Nov. 30, 1988; and European Patent Application Publication No. 0 325 849, all incorporated herein by reference) was nick-translated and used to screen a rat brain cDNA library (see DNA Cloning, A practical approach, Vol I and II, D. M. Glover, ed. (IRL Press (1985)) and a lambda-gt11 human liver cDNA library (Kwok et al., Biochem. 24: 556 (1985)) at low stringency. The hybridization mixture contained 35% formamide, 1× Denhardt's, 5× SSPE (1× SSPE=0.15M NaCl, 10 mM $Na_2HPO_4$ 1 mM EDTA), 0.1% SDS, 10% dextran sulfate, 100 µg/ml denatured salmon sperm DNA and $10^6$ cpm of ($^{32}P$)-labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

After several rounds of screening, a pure positive clone having an insert of about 2.1 kb is obtained from the rat brain cDNA library. Several positive clones are obtained from the human liver library. Sequence analysis of the positive rat brain clone indicates that this clone encodes a novel member of the steroid/thyroid superfamily of receptors. Sequence analysis of one of the positive human liver clones (designated "hL1", a 1.7 kb cDNA) indicates that this clone is the human equivalent of the rat brain clone, based on sequence homology.

The EcoRI insert of clone hL1 (labeled with $^{32}P$) is also used as a probe to screen a human testis cDNA library (Clonetech) and a human retina cDNA library (see Nathans et al., in Science 232: 193–202 (1986)). Hybridization conditions comprised a hybridization mixture containing 50% formamide, 1× Denhardt's, 5× SSPE, 0.1% SDS, 100 µg/ml denatured salmon sperm DNA and $10^6$ cpm of ($^{32}P$) -labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

After several rounds of screening, five (5) positive clones were obtained from the human retina cDNA library, and five (5) positive clones were obtained from the human testis cDNA library. Sequence analysis of two clones from the testis library indicates that these clones encode different isoforms of the same novel member of the steroid/thyroid superfamily of receptors (designated as "Verht19" and "Verht3"). Sequence analysis of one of the positive clones from the human retina library indicates that this clone is yet another isoform of the same novel member of the steroid/thyroid superfamily of receptors (designated "Verhr5"). The full length sequence of Verht19 is set forth herein as Sequence ID No. 1 (which includes an indication of where the splice site is for each of the variants, verht3 and verhr5). The amino-terminal sequence of verht3 and verhr5 are presented in Sequence ID Nos. 3 and 5, respectively. In addition, the interrelationship between each of these three isoforms is illustrated schematically in FIG. 1.

Example II

ISOLATION AND CHARACTERIZATION OF XR2

The KpnI/SacI restriction fragment (503bp) including the DNA-binding domain of hRAR-alpha-encoding DNA (See Giguere et al., Nature 330: 624 (1987); and commonly assigned U.S. patent application Ser. No. 276,536; now U.S. Pat. No. 4,981,784; filed Nov. 30, 1988; and European Patent Application Publication No. 0 325 849, all incorporated herein by reference) was nick-translated and used to screen a lambda-gt11 human liver cDNA library (Kwok et al., Biochem. 24: 556 (1985)) at low stringency. The hybridization mixture contained 35% formamide, 1× Denhardt's, 5× SSPE (1× SSPE=0.15M NaCl, 10 mM Na$_2$HPO$_4$, 1 mM EDTA), 0.1% SDS, 10% dextran sulfate, 100 mg/ml denatured salmon sperm DNA and 10$^6$ cpm of ($^{32}$P)-labelled probe. Duplicate nitrocellulose filters were hybridized for 16h at 42° C., washed once at 25° C. for 15 min with 2× SSC (1× SSC=0.15M NaCl, 0.015 M sodium citrate), 0.1% SDS and then washed twice at 55° C. for 30 min. in 2× SSC, 0.1% SDS. The filters were autoradiographed for 3 days at −70° C. using an intensifying screen.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs (Devereux et al., Nucl. Acids Res. 12, 387 (1984)). Several clones of a unique receptor-like sequence were identified, the longest of which was designated lambda-HL1-1 (also referred to herein as XR2).

The DNA sequence of the resulting clone is set forth as Sequence ID No. 7.

Example III

ISOLATION AND CHARACTERIZATION OF XR4

A clone which encodes a portion of the coding sequence for XR4 was isolated from a mouse embryonic library by screening under low stringency conditions (as described above).

The library used was a lambda gt10 day 8.5 cDNA library having an approximate titer of 1.3×10$^{10}$/ml (derived from 8.5 day old embryonic material with as much of the amnion and extraembryonic tissues dissected away as possible). This library was prepared from poly A+ selected RNA (by oligo-dT priming), Gubler & Hoffman cloning methods (Gene 25: 263 (1983)), and cloned into the EcoRI site of lambda gt10.

The probe used was a mixture of radioactively labeled DNA derived from the DNA binding regions of the human alpha and beta retinoic acid receptors.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs (Devereux et al., Nucl. Acids Res. 12, 387 (1984)). Several clones of a unique receptor-like sequence were identified, the longest of which was designated XR4.

The DNA sequence of the resulting clone is set forth as Sequence ID No. 9.

Example IV

ISOLATION AND CHARACTERIZATION OF XR5

A clone which encodes a portion of the coding sequence for XR5 was isolated from a mouse embryonic library by screening under low stringency conditions (as described above).

The library used was the same lambda gt10 day 8.5 cDNA library described in the preceding example. Similarly, the probe used was the same mixture of radioactively labeled DNA described in the preceding example.

Only one of the clones isolated corresponds to a portion of the coding region for XR5. A 0.7 kb EcoRI fragment of this clone (designated as No. II-17) was subcloned into the bluescript pksII-Vector. Partial sequence analysis of this insert fragment shows homology to the DNA binding domain of the retinoic acid receptors.

The EcoRI-insert was used to rescreen a second library (a mouse lambda ZAPII day 6.5 cDNA library, prepared as described below) under high stringency conditions. A total of 21 phages were isolated and rescued into the psk-vector. Partial sequencing allowed inserts from 13 of these phages to be identified as having sequences which overlap with XR5 II-17. The clone with the longest single EcoRI-insert was sequenced, revealing an open reading frame of 556 amino acids. This sequence was extended further upstream by 9bp from the furthest 5'-reaching clone.

The DNA sequence of the resulting clone is set forth as Sequence ID No. 11.

The day 6.5 cDNA library, derived from 6.5 day old mouse embryonic material was prepared from poly A+ selected RNA (by oligo-dT priming), and cloned into the EcoRI site of lambda gt10.

Example V

ISOLATION AND CHARACTERIZATION OF XR79

The 550 bp BamHI restriction fragment, including the DNA-binding domain of mouse RAR-beta-encoding DNA (See Hamada et al., Proc. Natl. Acad. Sci. 86: 8289 (1989); incorporated by reference herein) was nick-translated and used to screen a Lambda-ZAP cDNA library comprising a size selected Drosophila genomic library (~2-5 kb, EcoRI restricted) at low stringency. The hybridization mixture contained 35% formamide, 1× Denhardt's, 5× SSPE (1× SSPE=0.15M NaCl, 10 mM Na$_2$HPO$_4$ 1 mM EDTA), 0.1% SDS, 10% dextran sulfate, 100 mg/ml denatured salmon sperm DNA and 10$^6$ cpm of ($^{32}$P)-labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

After several rounds of screening, a pure positive clone having an insert of about 3.5 kb is obtained from the Drosophila genomic library. This genomic clone was then used to screen a Drosophila imaginal disc lambda gt10 cDNA library (obtained from Dr. Charles Zuker; see DNA Cloning, A practical approach, Vol I and II, D. M. Glover, ed. (IRL Press (1985)). Hybridization conditions comprised a hybridization mixture containing 50% formamide, 1× Denhardt's, 5× SSPE, 0.1% SDS, 100 µg/ml denatured salmon sperm DNA and 10$^6$ cpm of ($^{32}$P)-labelled probe. Duplicate nitrocellulose filters were hybridized for 16h at 42° C., washed once at 25° C. for 15 min with 2× SSC (1× SSC=0.15M NaCl, 0.015M sodium citrate), 0.1% SDS and then washed twice at 55° C. for 30 min. in 2× SSC, 0.1% SDS. The filters were autoradiographed for 3 days at −70° C. using an intensifying screen.

Sequence analysis of the positive cDNA clone indicates that this clone encodes another novel member of the steroid/ thyroid superfamily of receptors (designated "XR79", a 2.5 kb cDNA) See Sequence ID No. 13 for the DNA sequence of the resulting clone.

The 2.5 kb cDNA encoding XR79 was nick-translated and used as a probe for a nitrocellulose filter containing size-fractionated total RNA, isolated by standard methods from Drosophila melanogaster of different developmental stages. The probe hybridized to a 2.5 kb transcript which was present in RNA throughout development. The levels were highest in RNA from 0–3 hour old embryos and lowest in RNA from second instar larvae. The same 2.5 kb cDNA was nick translated using biotinylated nucleotides and used as a probe for in situ sybridization to whole Drosophila embryos (Tautz and Pfeifle, Chromosoma 98: 81–85 (1989)). The RNA distribution appeared relatively uniform at different stages of embryogenesis.

Example VI

SEQUENCE COMPARISONS OF INVENTION RECEPTORS WITH hRARα, hTRβ, hGR, AND hRXRα

Amino acid sequences of XR1, hRAR-alpha (human retinoic acid receptor-alpha), hTR-beta (human thyroid hormone receptor-beta), hGR (human glucocorticoid receptor), and hRXR-alpha (human retinoid receptor-alpha) were aligned using the University of Wisconsin Genetics Computer Group program "Bestfit" (Devereux et al., supra). The percentage of amino acid identity between RX2 and the other receptors, i.e., in the 66–68 amino acid DNA binding domains and the ligand-binding domains, are summarized in Table 1 as percent amino acid identity.

TABLE 1

Percent amino acid identity between receptor XR1 (verht19) and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 21 | 45 | 20 |
| hTRβ | 31 | 14 | 59 | 30 |
| hRARα | 32 | 25 | 68 | 27 |
| hRXRα | 29 | 15 | 65 | 22 |

[1]"N-term" = amino terminal domain
[2]"DNA-BD" = receptor DNA binding domain
[3]"Ligand-BD" = receptor ligand binding domain Similarly, the amino acid sequences of invention receptors XR2, XR4, XR5, and XR79 were compared with human RAR-alpha (hRARα), human TR-beta (hTRβ), human glucocorticoid (hGR) and human RXR-alpha (hRXRα). As done in Table 1, the percentage of amino acid identity between the invention receptors and the other receptors are summarized in Tables 2–5, respectively.

TABLE 2

Percent amino acid identity between receptor XR2 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 24 | 21 | 50 | 20 |
| hTRβ | 31 | 19 | 56 | 29 |

TABLE 2-continued

Percent amino acid identity between receptor XR2 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hRARα | 33 | 21 | 55 | 32 |
| hRXRα | 27 | 19 | 52 | 23 |

[1]"N-term" = amino terminal domain
[2]"DNA-BD" = receptor DNA binding domain
[3]"Ligand-BD" = receptor ligand binding domain

TABLE 3

Percent amino acid identity between receptor XR4 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 25 | 24 | 48 | 21 |
| hTRβ | 31 | 21 | 58 | 27 |
| hRARα | 32 | 22 | 62 | 29 |
| hRXRα | 33 | 24 | 62 | 28 |

[1]"N-term" = amino terminal domain
[2]"DNA-BD" = receptor DNA binding domain
[3]"Ligand-BD" = receptor ligand binding domain

TABLE 4

Percent amino acid identity between receptor XR5 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 20 | 20 | 44 | 20 |
| hTRβ | 24 | 14 | 52 | 22 |
| hRARα | 27 | 19 | 59 | 19 |
| hRXRα | 29 | 17 | 61 | 27 |

[1]"N-term" = amino terminal domain
[2]"DNA-BD" = receptor DNA binding domain
[3]"Ligand-BD" = receptor ligand binding domain

TABLE 5

Percent amino acid identity between receptor XR79 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 22 | 50 | 20 |
| hTRβ | 28 | 22 | 55 | 20 |
| hRARα | 24 | 14 | 59 | 18 |
| hRXRα | 33 | 20 | 65 | 24 |

[1]"N-term" = amino terminal domain
[2]"DNA-BD" = receptor DNA binding domain
[3]"Ligand-BD" = receptor ligand binding domain While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding novel receptor of the present invention designated as "hXR1".

Sequence ID No. 2 is the amino acid sequence deduced from the nucleotide sequence set forth in Sequence ID No. 1 (variously referred to herein as receptor "XR1", "hXR1", "hXR1.pep" or "verHT19.pep").

Sequence ID No. 3 is a nucleotide sequence encoding the amino-terminal portion of the novel receptor of the present invention designated as "hXR1prime".

Sequence ID No. 4 is the amino acid sequence deduced from the nucleotide sequence set forth in Sequence ID No. 3 (variously referred to herein as receptor "XR1prime", "hXR1prime", "hXR1prime.pep" or "verHT3.pep").

Sequence ID No. 5 is a nucleotide sequence encoding the amino-terminal portion of the novel receptor of the present invention designated as "hXR1prim2".

Sequence ID No. 6 is the amino acid sequence deduced from the nucleotide sequence set forth in Sequence ID No. 5 (variously referred to herein as receptor "XR1prim2", "hXR1prim2", "hXR1prim2.pep" or "verHr5.pep").

Sequence ID No. 7 is a nucleotide sequence encoding the novel receptor of the present invention designated as "hXR2".

Sequence ID No. 8 is the amino acid sequence deduced from the nucleotide sequence set forth in Sequence ID NO. 7 (variously referred to herein as receptor "XR2", "hXR2" or "hXR2.pep").

Sequence ID No. 9 is a nucleotide sequence encoding novel receptor of the present invention referred to herein as "mXR4".

Sequence ID No. 10 is the amino acid sequence deduced from the nucleotide sequence of Sequence ID No. 9 (variously referred to herein as receptor "XR4", "mXR4" or "mXR4.pep").

Sequence ID No. 11 is the nucleotide sequence encoding the novel receptor of the present invention referred to as "mXR5".

Sequence ID No. 12 is the amino acid sequence deduced from the nucleotide sequence of Sequence ID No. 11 (variously referred to herein as receptor "XR5", "mXR5" or "mXR5.pep").

Sequence ID No. 13 is the nucleotide sequence encoding the novel receptor of the present invention referred to as "dXR79".

Sequence ID No. 14 is the amino acid sequence deduced from the nucleotide sequence of Sequence ID No. 13 (variously referred to herein as "XR79", "dXR79" or "dXR79.pep").

That which is claimed is:

1. A polypeptide characterized by having a DNA binding domain comprising about 66 amino acids with 9 Cys residues, wherein said DNA binding domain is further characterized by the following amino acid sequence identity, relative to the DNA binding domains of hRAR-alpha, hTR-beta, hGR and hRXR-alpha, respectively:
   A. (i) about 68% amino acid sequence identity with the DNA binding domain of hRAR-alpha;
   (ii) about 59% amino acid sequence identity with the DNA binding domain of hTR-beta;
   (iii) about 45% amino acid sequence identity with the DNA binding domain of hGR; and
   (iv) about 65% amino acid sequence identity with the DNA binding domain of hRXR-alpha; or
   B. (i) about 55% amino acid sequence identity with the DNA binding domain of hRAR-alpha;
   (ii) about 56% amino acid sequence identity with the DNA binding domain of hTR-beta;
   (iii) about 50% amino acid sequence identity with the DNA binding domain of hGR; and
   (iv) about 52% amino acid sequence identity with the DNA binding domain of hRXR-alpha; or
   C. (i) about 62% amino acid sequence identity with the DNA binding domain of hRAR-alpha;
   (ii) about 58% amino acid sequence identity with the DNA binding domain of hTR-beta;
   (iii) about 48% amino acid sequence identity with the DNA binding domain of hGR; and
   (iv) about 62% amino acid sequence identity with the DNA binding domain of hRXR-alpha; or
   D. (i) about 59% amino acid sequence identity with the DNA binding domain of hRAR-alpha;
   (ii) about 52% amino acid sequence identity with the DNA binding domain of hTR-beta;
   (iii) about 44% amino acid sequence identity with the DNA binding domain of hGR; and
   (iv) about 61% amino acid sequence identity with the DNA binding domain of hRXR-alpha; or
   E. (i) about 59% amino acid sequence identity with the DNA binding domain of hRAR-alpha;
   (ii) about 55% amino acid sequence identity with the DNA binding domain of hTR-beta;
   (iii) about 50% amino acid sequence identity with the DNA binding domain of hGR; and
   (iv) about 65% amino acid sequence identity with the DNA binding domain of hRXR-alpha.

2. A polypeptide according to claim 1 wherein the DNA binding domain of said polypeptide has:
   (i) about 68% amino acid sequence identity with the DNA binding domain of hRAR-alpha;
   (ii) about 59% amino acid sequence identity with the DNA binding domain of hTR-beta;
   (iii) about 45% amino acid sequence identity with the DNA binding domain of hGR; and
   (iv) about 65% amino acid sequence identity with the DNA binding domain of hRXR-alpha.

3. A polypeptide according to claim 2 wherein the ligand binding domain of said polypeptide has:
   (i) about 27% amino acid sequence identity with the ligand binding domain of hRAR-alpha;
   (ii) about 30% amino acid sequence identity with the ligand binding domain of hTR-beta;
   (iii) about 20% amino acid sequence identity with the ligand binding domain of hGR; and
   (iv) about 22% amino acid sequence identity with the ligand binding domain of hRXR-alpha.

4. A polypeptide according to claim 3 wherein said polypeptide has an overall amino acid sequence identity of:
   (i) about 32% relative to hRAR-alpha;
   (ii) about 31% relative to hTR-beta;
   (iii) about 18% relative to hGR; and
   (iv) about 29% relative to hRXR-alpha.

5. A polypeptide according to claim 1 wherein the DNA binding domain of said polypeptide has:
   (i) about 55% amino acid sequence identity with the DNA binding domain of hRAR-alpha;
   (ii) about 56% amino acid sequence identity with the DNA binding domain of hTR-beta;
   (iii) about 50% amino acid sequence identity with the DNA binding domain of hGR; and
   (iv) about 52% amino acid sequence identity with the DNA binding domain of hRXR-alpha.

6. A polypeptide according to claim 5 wherein the ligand binding domain of said polypeptide has:
   (i) about 32% amino acid sequence identity with the ligand binding domain of hRAR-alpha;
   (ii) about 29% amino acid sequence identity with the ligand binding domain of hTR-beta;
   (iii) about 20% amino acid sequence identity with the ligand binding domain of hGR; and
   (iv) about 23% amino acid sequence identity with the ligand binding domain of hRXR-alpha.

7. A polypeptide according to claim 6 wherein said polypeptide has an overall amino acid sequence identity of:
   (i) about 33% relative to hRAR-alpha;
   (ii) about 31% relative to hTR-beta;
   (iii) about 24% relative to hGR; and
   (iv) about 27% relative to hRXR-alpha.

8. A polypeptide according to claim 1 wherein the DNA binding domain of said polypeptide has:
   (i) about 62% amino acid sequence identity with the DNA binding domain of hRAR-alpha;
   (ii) about 58% amino acid sequence identity with the DNA binding domain of hTR-beta;
   (iii) about 48% amino acid sequence identity with the DNA binding domain of hGR; and
   (iv) about 62% amino acid sequence identity with the DNA binding domain of hRXR-alpha.

9. A polypeptide according to claim 8 wherein the ligand binding domain of said polypeptide has:
  (i) about 29% amino acid sequence identity with the ligand binding domain of hRAR-alpha;
  (ii) about 27% amino acid sequence identity with the ligand binding domain of hTR-beta;
  (iii) about 21% amino acid sequence identity with the ligand binding domain of hGR; and
  (iv) about 28% amino acid sequence identity with the ligand binding domain of hRXR-alpha.

10. A polypeptide according to claim 9 wherein said polypeptide has an overall amino acid sequence identity of:
  (i) about 32% relative to hRAR-alpha;
  (ii) about 31% relative to hTR-beta;
  (iii) about 25% relative to hGR; and
  (iv) about 33% relative to hRXR-alpha.

11. A polypeptide according to claim 1 wherein the DNA binding domain of said polypeptide has:
  (i) about 59% amino acid sequence identity with the DNA binding domain of hRAR-alpha;
  (ii) about 52% amino acid sequence identity with the DNA binding domain of hTR-beta;
  (iii) about 44% amino acid sequence identity with the DNA binding domain of hGR; and
  (iv) about 61% amino acid sequence identity with the DNA binding domain of hRXR-alpha.

12. A polypeptide according to claim 11 wherein the ligand binding domain of said polypeptide has:
  (i) about 19% amino acid sequence identity with the ligand binding domain of hRAR-alpha;
  (ii) about 22% amino acid sequence identity with the ligand binding domain of hTR-beta;
  (iii) about 20% amino acid sequence identity with the ligand binding domain of hGR; and
  (iv) about 27% amino acid sequence identity with the ligand binding domain of hRXR-alpha.

13. A polypeptide according to claim 12 wherein said polypeptide has an overall amino acid sequence identity of:
  (i) about 27% relative to hRAR-alpha;
  (ii) about 24% relative to hTR-beta;
  (iii) about 20% relative to hGR; and
  (iv) about 29% relative to hRXR-alpha.

14. A polypeptide according to claim 1 wherein the DNA binding domain of said polypeptide has:
  (i) about 59% amino acid sequence identity with the DNA binding domain of hRAR-alpha;
  (ii) about 55% amino acid sequence identity with the DNA binding domain of hTR-beta;
  (iii) about 50% amino acid sequence identity with the DNA binding domain of hGR; and
  (iv) about 65% amino acid sequence identity with the DNA binding domain of hRXR-alpha.

15. A polypeptide according to claim 14 wherein the ligand binding domain of said polypeptide has:
  (i) about 18% amino acid sequence identity with the ligand binding domain of hRAR-alpha;
  (ii) about 20% amino acid sequence identity with the ligand binding domain of hTR-beta;
  (iii) about 20% amino acid sequence identity with the ligand binding domain of hGR; and
  (iv) about 24% amino acid sequence identity with the ligand binding domain of hRXR-alpha.

16. A polypeptide according to claim 15 wherein said polypeptide has an overall amino acid sequence identity of:
  (i) about 24% relative to hRAR-alpha;
  (ii) about 28% relative to hTR-beta;
  (iii) about 18% relative to hGR; and
  (iv) about 33% relative to hRXR-alpha.

17. A polypeptide according to claim 1 wherein the ligand binding domain of said polypeptide is further characterized by the following amino acid sequence identity, relative to the ligand binding domains of hRAR-alpha, hTR-beta, hGR and hRXR-alpha, respectively:
  A (i) about 27% amino acid sequence identity with the ligand binding domain of hRAR-alpha;
    (ii) about 30% amino acid sequence identity with the ligand binding domain of hTR-beta;
    (iii) about 20amino acid sequence identity with the ligand binding domain of hGR; and
    (iv) about 22% amino acid sequence identity with the ligand binding domain of hRXR-alpha; or
  B. (i) about 32% amino acid sequence identity with the ligand binding domain of hRAR-alpha;
    (ii) about 29% amino acid sequence identity with the ligand binding domain of hTR-beta;
    (iii) about 20% amino acid sequence identity with the ligand binding domain of hGR; and
    (iv) about 23% amino acid sequence identity with the ligand binding domain of hRXR-alpha; or
  C. (i) about 29% amino acid sequence identity with the ligand binding domain of hRAR-alpha;
    (ii) about 27% amino acid sequence identity with the ligand binding domain of hTRt-beta;
    (iii) about 21% amino acid sequence identity with the ligand binding domain of hGR; and
    (iv) about 28% amino acid sequence identity with the ligand binding domain of hRXR-alpha; or
  D. i) about 19% amino acid sequence identity with the ligand binding domain of hRAR-alpha;
    (ii) about 22% amino acid sequence identity with the ligand binding domain of hTR-beta;
    (iii) about 20% amino acid sequence identity with the ligand binding domain of hGR; and
    (iv) about 27% amino acid sequence identity with the ligand binding domain of hRXR-alpha; or
  E. (i) about 18% amino acid sequence identity with the ligand binding domain of hRAR-alpha;
    (ii) about 20% amino acid sequence identity with the ligand binding domain of hTR-beta;
    (iii). about 20% amino acid sequence identity with the ligand binding domain of hGR; and
    (iv) about 24% amino acid sequence identity with the ligand binding domain of hRXR-alpha.

18. A polypeptide according to claim 1 wherein said polypeptide has an overall amino acid sequence identity, relative to hRAR-alpha, hTR-bea, hGR and hRXR-alpha, respectively of:
  A. (i) about 32% relative to hRAR-alpha;
    (ii) about 31% relative to hTR-beta;
    (iii) about 18% relative to hGR; and
    (iv) about 29% relative to hRXR-alpha; or
  B. (i) about 33% relative to hRAR-alpha;
    (ii) about 31% relative to hTR-beta;

(iii) about 24% relative to hGR; and
(iv) about 27 relative to hRXR-alpha; or
C. (i) about 32 relative to hRAR-alpha.
(ii) about 31% relative to hTR-beta;
(iii) about 25% relative to hGR; and
(iv) about 33% relative to hRXR-alpha; or
D. (i) about 27% relative to hRAR-alpha;
(ii) about 24% relative to hTR-beta;
(iii) about 20% relative to hGR; and
(iv) about 29 relative to hRXR-alpha; or
E. (i) about 24% relative to hRAR-alpha;
(ii) about 28% relative to hTR-beta;
(iii) about 18% relative to hGR; and
(iv) about 33 relative to hRXR-alpha.

19. A polypeptide according to claim 1 wherein said polypeptide has the same amino acid sequence as polypeptides selected from SEQ ID NOS:2, 4, 6, 8, 10, 12 or 14.

20. A chimeric receptor comprising an amino-terminal domain, a DNA-binding domain, and a ligand-binding domain, wherein at least one of the domains thereof is derived from the polypeptide of claim 1; and wherein at least one of the domains thereof is derived from at least one previously identified member of the steroid/thyroid superfamily of receptors.

* * * * *